United States Patent
Nakamoto et al.

(10) Patent No.: US 7,524,875 B2
(45) Date of Patent: Apr. 28, 2009

(54) MODIFIED BIO-RELATED SUBSTANCE, PROCESS FOR PRODUCING THE SAME, AND INTERMEDIATE

(75) Inventors: Ken-ichiro Nakamoto, Kanagawa (JP); Syunsuke Ohashi, Kanagawa (JP); Yuji Yamamoto, Tokyo (JP); Kenji Sakanoue, Kanagawa (JP); Chika Itoh, Kanagawa (JP); Tohru Yasukohchi, Kanagawa (JP)

(73) Assignee: NOF Corporation, Tokyo (JP)

( * ) Notice: Subject to any disclaimer, the term of this patent is extended or adjusted under 35 U.S.C. 154(b) by 439 days.

(21) Appl. No.: 11/142,255

(22) Filed: Jun. 2, 2005

(65) Prior Publication Data
US 2005/0288490 A1   Dec. 29, 2005

Related U.S. Application Data

(63) Continuation-in-part of application No. 10/716,432, filed on Nov. 20, 2003.

(30) Foreign Application Priority Data
Nov. 20, 2002 (JP) ............ P. 2002-337113

(51) Int. Cl.
  *A61K 31/075* (2006.01)
  *A61K 31/4015* (2006.01)
  *A61K 31/4164* (2006.01)
  *A61K 31/4192* (2006.01)
  *C07C 43/11* (2006.01)
  *C07D 207/444* (2006.01)
  *C07D 233/64* (2006.01)
  *C07D 249/04* (2006.01)
  *C07D 487/06* (2006.01)

(52) U.S. Cl. .............. 514/359; 514/385; 514/718; 548/255; 548/334.1; 548/530; 568/625

(58) Field of Classification Search ............. 568/625; 514/359, 385, 425, 718; 548/255, 334.1, 548/530
See application file for complete search history.

(56) References Cited

U.S. PATENT DOCUMENTS 6,667,292 B1   12/2003   Kitabatake et al.

FOREIGN PATENT DOCUMENTS

| JP | 6-145341 A | 5/1994 |
| JP | 8-59818 A | 3/1996 |
| JP | 11-228685 A | 8/1999 |
| JP | 2000-1541 A | 1/2000 |
| JP | 2003-113241 A | 4/2003 |

*Primary Examiner*—Taofiq A Solola
(74) *Attorney, Agent, or Firm*—Sughrue Mion, PLLC

(57) ABSTRACT

A modified bio-related substance, wherein at least one poly(alkylene glycol)oxy group represented by the following formula (1) is combined in a molecule:

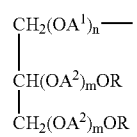

(1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, and the groups represented by $OA^2$ are the same or different from each other in one molecule, n and m are each average number of moles of the oxyalkylene group added, n represents 0 to 1000, and m represents 10 to 1000.

29 Claims, 5 Drawing Sheets

(A)  (B)  (C)

SEQUENCE LISTING

<160> NUMBER OF SEQ ID NOS: 1

<210> SEQ ID NO 1
<211> LENGTH: 24
<212> TYPE: PRT
<213> ORGANISM: Homo sapiens

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

MODIFIED BIO-RELATED SUBSTANCE, PROCESS FOR PRODUCING THE SAME, AND INTERMEDIATE

This is a Continuation-In-Part application which claims priority under 35 U.S.C §120 to application Ser. No. 10/716,432 filed in the United States on Nov. 20, 2003; the entire content of which is hereby incorporated by reference.

TECHNICAL FIELD

The present invention relates to a bio-related substance modified by the bonding to a polyalkylene glycol derivative, a process for producing the same, and a reactive polyalkylene glycol derivative which is an intermediate thereof.

BACKGROUND ART

Recently, a large number of proteins, polypeptides, synthetic compounds, and compounds extracted from natural resources having physiological activity and the application thereof to pharmaceuticals has been extensively studied. However, these physiologically active substances have short half-lives in blood when they are injected to a body and hence it is difficult to obtain a sufficient pharmacological effect. This is because the physiologically active substances injected to a body are usually cleared from the body because of the filtration through glomeruli in the kidney and the uptake by macrophages in the liver and spleen. Therefore, it is attempted to improve the behavior in a body by including these physiologically active substances in liposomes or polymer micelles or increasing their molecular weight through chemical modification with polyethylene glycol which is an amphipathic polymer. Polyethylene glycol exhibits a low interaction with the other bio-components owing to its steric repulsion effect and as a result, proteins and polypeptides such as enzymes modified with polyethylene glycol exhibit an effect of avoiding the filtration through glomeruli in the kidney and bio-reactions such as immunoreaction, so that they achieve half-lives in blood longer than those of unmodified substances. Moreover, they also have decreased toxicity and antigenicity and further exhibit an effect of enhancing the solubility of a sparingly water-soluble compound having a high hydrophobicity.

Hitherto, in the case of modifying a physiologically active substance with polyethylene glycol, particularly in the case of modifying a low-molecular-weight drug or peptide, there arises a problem that few reactive functional groups can be used for the modification with polyethylene glycol. Furthermore, when a peptide or drug is modified with many polyethylene glycol molecules for obtaining a sufficient effect of the modification with polyethylene glycol, the active site of the peptide or drug is blocked and hence problems may arise that its own function and efficacy cannot be exhibited sufficiently and enough solubility in water cannot be obtained.

For solving such problems, the reduction of the number of modification with polyethylene glycol using a branched polyethylene glycol derivative has been attempted. JP-B-61-42558 proposes a polyethylene glycol-modified L-asparaginase. However, cyanuric chloride as a starting material for a reactive polyethylene glycol derivative has three reactive sites and hence it is difficult to introduce two polyethylene glycol chains thereinto selectively. Accordingly, it is difficult to synthesize a highly pure polyethylene glycol-modified L-asparaginase.

Also, JP-A-10-67800 proposes a polyethylene glycol-modified interferon α. However, this substance has three urethane and amide bonds including the linkage between interferon α and the poly(ethylene glycol)oxy group. These bonds are labile to hydrolysis during storage or during the reaction under an alkaline condition and as a result, there arises a problem that the branched polyethylene glycol moiety is decomposed to a single chain. This is because the polyethylene glycol derivative which is the intermediate material has been produced by a method wherein two monomethoxypolyethylene glycols and amino groups at α- and ε-positions of lysine are combined through urethane bonds and then the carboxyl residue of lysine is converted into a succinimide ester. In addition, in order to produce the polyethylene glycol-modified interferon α, there arises a problem that increased impurities are produced owing to the multi-step process, such as the activation of the terminal hydroxyl groups of two monomethoxypolyethylene glycols, the combination with lysine, the activation of the carboxyl residue of lysine, and the combination with interferon α.

Accordingly, it is desired to develop a bio-related substance formed by highly stable bonds, a process for producing the same, and a branched reactive polyalkylene glycol derivative which can be produced in a convenient manner and in a high purity and has a higher stability.

DISCLOSURE OF THE INVENTION

A first object of the invention is to provide a bio-related substance having a branched poly(alkylene glycol)oxy group which is formed by stable bonds and is hardly decomposed to a single chain, and a process for producing the same.

A second object of the invention is to provide a polyalkylene glycol derivative having a reactive group, which can be combined with a bio-related substance, at the primary carbon at the 1-position of the glycerin skeleton and having polyalkylene glycol chains at the 2- and 3-positions.

As a result of extensive studies for solving the above problems, the present inventors have found out a novel bio-related substance having a branched poly(alkylene glycol)oxy group, a process for producing the same, and a polyalkylene glycol derivative as an intermediate thereof, and thus accomplished the invention.

Namely, the invention relates to a modified bio-related substance, wherein at least one poly(alkylene glycol)oxy group represented by the following formula (1):

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, and the groups represented by $OA^2$ are the same or different from each other in one molecule, n and m are each average number of moles of the oxyalkylene group added, n represents 0 to 1000, and m represents 10 to 1000, is combined in a molecule.

Moreover, the invention relates to an intermediate for the modified bio-related substance, which is represented by the following formula (2):

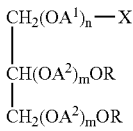

(2)

wherein R, $OA^1$, $OA^2$, n, and m are the same as above, and X represents a functional group capable of chemically reacting with a bio-related substance.

Furthermore, the invention relates to a process for producing a modified bio-related substance wherein at least one poly(alkylene glycol)oxy group represented by the formula (1) is combined in a molecule, comprising a step of combining the above intermediate with a bio-related substance.

In addition, the invention relates to a compound of the formula (p) as a starting material of the compound of the formula (2) and a process for producing the same.

The modified bio-related substance of the invention is formed by stable bonds and is hardly decomposed to a single chain. Moreover, the invention can provide a polyalkylene glycol derivative having a reactive group, which can be combined with a bio-related substance, at the primary carbon at the 1-position of the glycerin skeleton and having polyalkylene glycol chains at the 2- and 3-positions.

BEST MODE FOR CARRYING OUT THE INVENTION

Figure 1:
FIG. 1 illustrates an experimental result by polyacrylamide gel electrophoresis of OVA and modified OVA.

The modified bio-related substance of the invention is a substance wherein a bio-related substance is combined with at least one poly(alkylene glycol)oxy group represented by the above formula (1).

R in the poly(alkylene glycol)oxy group of the formula (1) is a hydrocarbon group having 1 to 24 carbon atoms and specific hydrocarbon groups include hydrocarbon groups such as a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an oleyl group, a nonadecyl group, an eicosyl group, a heneicosyl group, docosyl group, a tricosyl group, a tetracosyl group, a benzyl group, a cresyl group, a butylphenyl group, and a dodecylphenyl group. The hydrocarbon group is preferably a hydrocarbon group having 1 to 10 carbon atoms, more preferably a methyl group or an ethyl group, further preferably a methyl group.

$OA^1$ and $OA^2$ represent each an oxyalkylene group having 2 to 4 carbon atoms. Specifically, they include an oxyethylene group, an oxypropylene group, an oxytrimethylene group, an oxy-1-ethylethylene group, an oxy-1,2-dimethylethylene group, and an oxytetramethylene group. The oxyalkylene groups may be the same or different from each other and may be added randomly or block-wise. In general, the fewer the carbon atoms are, the higher the hydrophilicity is. The group is preferably an oxyethylene group or an oxypropylene group, more preferably an oxyethylene group. m and n are each average number of moles of the oxyalkylene group added. m represents 10 to 1000, preferably 20 to 800, more preferably 50 to 800, most preferably 100 to 800. n represents 0 to 1000, preferably 0 to 500, more preferably 0 to 200, most preferably 0 to 50. In a preferable embodiment, n is 0. In another preferable embodiment, n is 1 to 50. In the latter case, n is particularly preferably 1 to 3.

The number of modifications with the poly(alkylene glycol)oxy group to the bio-related substance is not particularly limited but is preferably 1 to 100, more preferably 1 to 20.

The "bio-related substance" according to the invention means a substance relating to a body. The substances relating to a body include the following.

(1) Animal Cell-Constituting Materials such as Phospholipids, Glycolipids, and Glycoproteins The animal cell-constituting materials are components constituting cell membranes and the kind is not particularly limited but examples thereof include phospholipids, glycolipids, and glycoproteins. Examples of more specific phospholipids include phosphatidic acid, phosphatidylcholine, phosphatidylethanolamine, cardiolipin, phosphatidylserine, and phosphatidylinositol. In addition, lyso isomers thereof are also included. These phospholipids may be those derived from natural products such as egg yolk or soybean or may be synthesized products. The composition of fatty acids is not particularly limited but may include fatty acids having 12 to 22 carbon atoms. These fatty acids may be saturated fatty acids or may be those containing an unsaturated bond. Examples of more specific glycolipids include ceramides, cerebrosides, sphingosines, gangliosides, and glyceroglycolipids. In addition, fatty acids, monoglycerides, diglycerides, cholesterols, and bile acid are also included.

(2) Body Fluid-constituting Substances such as Blood, Lymph, and Bone Marrow Liquid The body fluid-constituting substances mean fluid components existing inside and outside cells and the kind is not particularly limited but examples thereof include blood, lymph, and bone marrow liquid. Examples of more specific body fluid-constituting components include hemoglobin, albumin, and blood coagulation factors.

(3) Physiologically Active Substances such as Vitamins, Neurotransmitters, Proteins, Polypeptides, and Drugs The physiologically active substances mean components controlling body functions and the kind is not particularly limited but examples thereof include vitamins, neurotransmitters, proteins, polypeptides, and drugs.

Examples of more specific vitamins include vitamin A, vitamin B, vitamin C, vitamin D, vitamin E, and vitamin K.

Examples of more specific neurotransmitters include adrenalin, noradrenalin, dopamine, acetylcholine, GABA, glutamic acid, and aspartic acid.

Examples of more specific proteins and polypeptides include the following. Hormones such as neurohypophysial hormone, thyroid hormone, male sex hormone, female sex hormone, and adrenal cortex hormone. Serum proteins such as hemoglobin and blood factors. Immunoglobulins such as IgG, IgE, IgM, IgA, and IgD. Cytokines and fragments thereof, such as interleukins (IL-1, IL-2, IL-3, IL-4, IL-5, IL-6, IL-7, IL-8, IL-9, IL-10, IL-11 and IL-12 subtypes), interferons (-α, -β, -γ), granulocyte-colony stimulating factors (α and β types), macrophage-colony stimulating factor, granulocyte-macrophage colony stimulating factor, platelet-derived growth factor, phospholipase-activating protein, insulin, glucagon, lectin, ricin, tumor necrosis factor, epidermal growth factor, transforming growth factors (-α, -β), fibroblast growth factor, hepatocyte growth factor, vascular endothelial growth factor, nerve growth factor, bone growth factor, insulin-like growth factor, heparin binding growth factor, tumor growth factor, glial cell line-derived neurotrophic factor, macrophage differentiating factor, differentiation-inducing factor, leukemia inhibitory factor, amphiregurin, somatomedin, erythropoietin, hemopoietin, thrombopoietin, and calcitonin. Enzymes such as proteolytic enzymes, oxidoreductases, transferases, hydrases, lyases, isomerases, ligases, asparaginases, arginases, arginine deaminases, adenosine deaminases, superoxide dismutases, endotoxinases, catalases, chymotrypsin, lipases, uricases, elastases, streptokinases, urokinases, prourokinases, adenosine diphosphatases, tyrosinases, bilirubin oxidases, glucose oxidases, glucodases, glactosidases, glucocerebrosidases, and glucouronidases. Monoclonal and polyclonal antibodies and fragments thereof. Polyamino acids such as poly-L-lysine, poly-D-lysine. Vaccines such as hepatitis B vaccine, malaria vaccine, melanoma vaccine, and HIV-1 vaccine, and antigens. In addition, glycoproteins are also included. Furthermore, also included are structurally similar substances having physiological activity similar to that of these physiologically active substances.

Moreover, these proteins and polypeptides may be isolated from natural sources thereof or cells subjected to genetic engineering or may be produced via various synthetic processes.

The drugs are not particularly limited but more preferably include anticancer drugs and antifungal drugs.

More specific anticancer drugs are not particularly limited but, for example, include paclitaxel, adriamycin, doxorubicin, cisplatin, daunomycin, mitomycin, vincristine, epirubicin, methotrexate, 5-fluorouracil, aclacinomycin, idamycin, bleomycin, pirarubicin, peplomycin, vancomycin, and camptothecine.

Specific antifungal drugs are not particularly limited but, for example, include amphotericin B, nystatin, flucytosine, miconazole, fluconazole, itraconazole, ketoconazole, and peptide antifungal drugs.

Moreover, these physiologically active substances also include flavonoids, terpenoids, carotenoids, saponins, steroids, quinones, anthraquinones, xanthones, coumarins, alkaloids, porphyrins, and polyphenols.

The intermediate for the bio-related substance of the invention is represented by the following formula (2).

(2)

In the formula, X is not particularly limited as far as it is a functional group or an unsaturated bond capable of forming a chemical bond with a bio-related substance. In a preferable embodiment, X is a group represented by the group (I), (II) or (III).

Group (I)

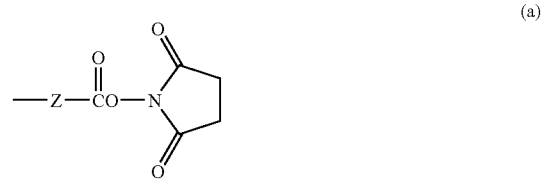

(a)

(b)

(c)

(d)

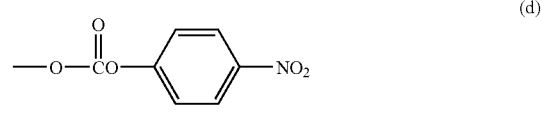

(e)

(f)

(h)

(i)

Group (II)

(g)

(j)

(k)

Group (III)

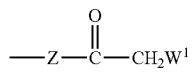  (xx1)

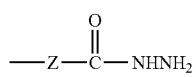  (xx2)

-Z-ONH$_2$  (xx3)

In the case of the reaction with an amino group of a bio-related substance, the groups represented by (a), (b), (d), (f), (h), (i), and (k) are preferable. In the case of the reaction with a mercapto group of a bio-related substance, the groups represented by (a), (b), (c), (d), (e), (f), (h), (i), (k), and (xx1) are preferable. In the case of the reaction with an unsaturated bond of a bio-related substance, the group represented by (c) is preferable. In the case of the reaction with a carboxyl group of a bio-related substance, the groups represented by (c), (g), and (j) are preferable. Moreover, in the case of the reaction with the aldehyde group of the bio-related substance, the groups represented by (c), (g), (j), (xx2), and (xx3) are preferable. In the case that the bio-related substance does not have any of an amino group, a mercapto group, an unsaturated bond, a carboxyl group, and an aldehyde group, these groups may be suitably introduced therein.

Z in the group (I), (II) or (III) is a linker between the poly(alkylene glycol)oxy group and the reactive functional group and is not particularly limited as far as it is a covalent bond, but preferably includes an alkylene group and an alkylene group containing an ester bond, a urethane bond, an amide bond, an ether bond, a carbonate bond, or a secondary amino group. Preferable alkylene group includes a methylene group, an ethylene group, a trimethylene group, a propylene group, an isopropylene group, a tetramethylene group, a butylene group, an isobutylene group, a pentamethylene group, and a hexamethylene group. More preferable is a structure of the following (z1). More preferable as an alkylene group containing an ester bond is a structure of the following (z2).

More preferable as an alkylene group containing an amide bond is a structure of the following (z3). A group of the following (z4), (Z7) and (z8) are more preferable as an alkylene group containing an ether bond. More preferable as an alkylene group containing a urethane bond is a structure of the following (z5). The following (z6) is a structure more preferable as an alkylene group containing a secondary amino group. s is defined for each formula independently, and s is an integer of 1 to 6, preferably an integer of 1 to 3, more preferably an integer of 2 to 3.

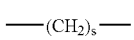  (z1)

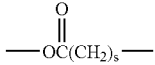  (z2)

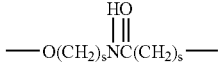  (z3)

  (z4)

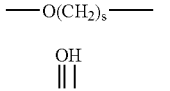  (z5)

  (z6)

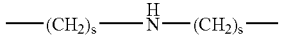  (z7)

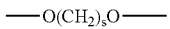  (z8)

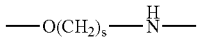

Y is a hydrocarbon group having 1 to 10 carbon atoms which may contain fluorine atom(s). Specifically, Y includes a methyl group, an ethyl group, a propyl group, an isopropyl group, a butyl group, a tert-butyl group, a hexyl group, a nonyl group, a vinyl group, a phenyl group, a benzyl group, a 4-methylphenyl group, a trifluoromethyl group, a 2,2,2-trifluoroethyl group, and a 4-(trifluoromethoxy)phenyl group, and is preferably a methyl group, a vinyl group, a 4-methylphenyl group, and a 2,2,2-trifluoroethyl group.

W$^1$ in the group (III) is a halogen atom selected from Cl, Br and I, and is preferably I.

In the compound represented by the formula (2), R, A$^1$O, A$^2$O, n, and m are the same as above.

Z, R, A$^1$O, A$^2$O, n, and m in the group (II) and the group (III) are also the same as above.

Tables 1, 2 and 6 show relation between a residual group T of the above bio-related substance and a functional group X of the poly(alkylene glycol)oxy group side which forms a chemical bond with the residual group T. In addition, Tables 1, 2 and 6 also show types of the chemical bonds between the poly(alkylene glycol)oxy groups and bio-related substances, which are formed by the reaction of the bio-related substances with X.

TABLE 1

| | Reactive group of physiologically active substance | | | | |
|---|---|---|---|---|---|
| X group | NH$_2$—T<br>Amino group | SH—T<br>Mercapto group | 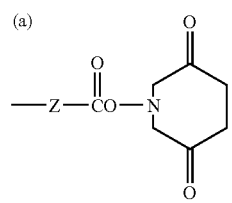—T<br>Unsaturated bond | HO—C(=O)—T<br>Carboxyl group | H—C(=O)—T<br>Aldehyde group |
| (a) 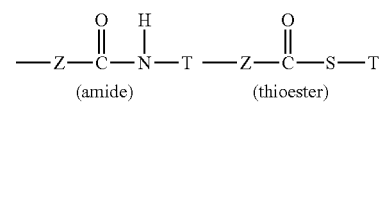 | —Z—C(=O)—N(H)—T<br>(amide) | —Z—C(=O)—S—T<br>(thioester) |  |  |  |

TABLE 1-continued

| X group | Reactive group of physiologically active substance | | | | |
|---|---|---|---|---|---|
| | NH$_2$—T Amino group | SH—T Mercapto group | —T Unsaturated bond | HO—C(=O)—T Carboxyl group | H—C(=O)—T Aldehyde group |
| (b) (OA$^1$)—O—S(=O)$_2$—Y | —(OA$^1$)—NH—T (secondary amino group) | (OA$^1$)—S—T (sulfide) | | | |
| (c) —Z—SH | | —Z—S—S—T (disulfide) | —Z—S—CH(CH$_3$)—CH$_2$—T (sulfide) | —Z—SC(=O)—T (thioester) | Z—S—C(—Z—S)—T (thioacetal) |
| (d) (OA$^1$)—OC(=O)O—C$_6$H$_4$—NO$_2$ | (OA$^1$)—OC(=O)NH—T (urethane) | (OA$^1$)—OC(=O)S—T (thiocarbonate) | | | |
| (e) —Z—N(maleimide) | | —Z—N(succinimide-S—T) (sulfide) | | | |

Note: In (b) and (d), X group is a moiety excluding (OA$^1$).

TABLE 2

| X group | Reactive group of physiologically active substance | | | | |
|---|---|---|---|---|---|
| | NH$_2$—T Amino group | SH—T Mercapto group | —T Unsaturated bond | HO—C(=O)—T Carboxyl group | H—C(=O)—T Aldehyde group |
| (f) —Z—CH(=O) | —Z—CH=N—T (Schiff base) →reduction→ —Z—CH$_2$—NH—T (secondary amino group) | —Z—C(OH)H—S—T (sulfide) | | | |
| (h) (OA$^1$)—OC(=O)—N(imidazole) | (OA$^1$)—OC(=O)NH—T (urethane) | (OA$^1$)—OC(=O)S—T thiocarbonate | | | |
| (i) (OA$^1$)—OC(=O)O—N(benzotriazole) | (OA$^1$)—OC(=O)NH—T (urethane) | (OA$^1$)—OC(=O)S—T (thiocarbonate) | | | |
| (g), (j), —Z—NH$_2$ | | | | —Z—NHC(=O)—T (amide) | —Z—CH=N—T (Schiff base) →reduction→ —Z—CH$_2$—NH—T (secondary amino group) |

TABLE 2-continued

| X group | Reactive group of physiologically active substance | | | | | |
|---|---|---|---|---|---|---|
| | NH$_2$—T Amino group | SH—T Mercapto group | ⸺T Unsaturated bond | HO—C(=O)—T Carboxyl group | H—C(=O)—T Aldehyde group | |
| (k) —Z—COOH | —Z—C(=O)—N(H)—T (amide) | —Z—C(=O)—S—T (thioester) | 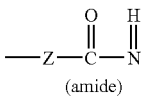 | 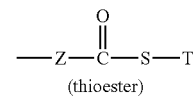 |  | |

Note: In (h) and (i), X group is a moiety excluding (OA$^1$).

TABLE 6

| X group | Reactive group of physiologically active substance | | | | |
|---|---|---|---|---|---|
| | NH$_2$—T Amino group | SH—T Mercapto group | ⸺T Unsaturated bond | HO—C(=O)—T Carboxyl group | H—C(=O)—T Aldehyde group |
| (xx1) —Z—C(=O)—CH$_2$W$^1$ | 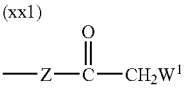 | —Z—C(=O)—CH$_2$—S—T (sulfide) | 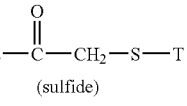 |  | 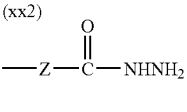 |
| (xx2) —Z—C(=O)—NHNH$_2$ |  | 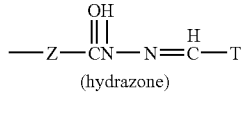 | 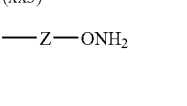 |  | —Z—C(OH)N—N=C(H)—T (hydrazone) |
| (xx3) —Z—ONH$_2$ | 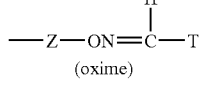 | | | | —Z—ON=C(H)—T (oxime) |

As is apparent from the tables, in the modified bio-related substances of the invention, the poly(alkylene glycol)oxy group and the bio-related substance are combined by, for example, an amide bond, a secondary amino group, a urethane bond, a thioester bond, a sulfide bond, a disulfide bond, a thiocarbonate bond, an oxime, a hydrazone bond, or a thioacetal bond.

The modified bio-related substances of the invention can be produced as follows.

(Case of Reacting an Amino Group of a Bio-related Substance with an Intermediate of the Invention)

In the case of the modification with an amino group of a bio-related substance, the intermediates (a), (b), (d), (f), (h), (i), and (k) of the invention are used. More preferably, (a), (b), (d), and (f) are used. At the reaction, the intermediates (a), (b), (d), (f), (h), (i), and (k) of the invention may be reacted in a ratio of equimolar or more to the bio-related substance. The reaction solvent is not particularly limited as far as it does not participate in the reaction, but in the case of reacting a protein or polypeptide, preferable solvents include buffer solutions such as phosphate buffer solutions, borate buffer solutions, Tris-acid buffer solutions, acetate buffer solutions, and carbonate buffer solutions. Furthermore, an organic solvent which does not deactivate the protein or polypeptide and does not participate in the reaction, such as acetonitrile, dimethyl sulfoxide, dimethylformamide, or dimethylacetamide, may be added. In the case of reacting an anticancer drug, antifungal drug, or phospholipid, preferable solvents include, in addition to the above buffer solutions, toluene, benzene, xylene, acetonitrile, ethyl acetate, diethyl ether, t-butyl methyl ether, tetrahydrofuran, chloroform, methylene dichloride, dimethyl sulfoxide, dimethylformamide, dimethylacetamide, water, methanol, ethanol, n-propanol, 2-propanol, and n-butanol. Also, the solvent need not be used. The order of adding the intermediate and the bio-related substance is optional. The reaction temperature is not particularly limited as far as it does not deactivate the bio-related substance, but the temperature is preferably 0 to 40° C. in the case of reacting a protein or polypeptide and is preferably −20 to 150° C. in the case of reacting an anticancer drug, antifungal drug, or phospholipid. The reaction time is preferably 0.5 to 72 hours, more preferably 1 to 24 hours. At the reaction, a condensing agent such as N,N'-dicyclohexylcarbodiimide (DCC) or 1-ethyl-3-(3-dimethylaminopropyl)carbodiimide hydrochloride (EDC) may be used. A covalent bond is formed between the bio-related substance and the intermediate of the invention by carrying out the reaction. An amide bond is formed in the case of using (a) or (k), a secondary amino group in the case of using (b), a urethane bond in the case of using (d), (h), or (i), and a Schiff base in the case of using (f). When a Schiff base is formed, it may be subjected to a reduction treatment using a reducing agent such as sodium cyanoborohydride to form a secondary amino group. After the reaction, the product may be purified by a purifying means such as dialysis, salting-out, ultrafiltration, ion-exchange chromatography, electrophoresis, extraction, recrystallization, adsorption treatment, reprecipitation, column chromatography, or supercritical extraction.

(Case of Reacting a Mercapto Group of a Bio-related Substance with an Intermediate of the Invention)

In the case of the modification with a mercapto group of a bio-related substance, the intermediates (a), (b), (c), (d), (e), (f), (h), (i), (k), and (xx1) of the invention are used. More preferably, (e) and (xx1) are used. The reaction solvent, reaction conditions, and the like are the same as in the case of using an amino group. At the reaction, a radical initiator such as iodine or AIBN may be used. A covalent bond is formed between the bio-related substance and the intermediate of the invention by carrying out the reaction, and a thioether bond is formed in the case of using (a) or (k), a thiocarbonate bond in the case of using (d), (h), or (i), a disulfide bond in the case of using (c), and a sulfide bond in the case of using (b), (e), (f), or (xx1).

(Case of Reacting an Unsaturated Bond of a Bio-related Substance with an Intermediate of the Invention)

In the case of the modification with an unsaturated bond of a bio-related substance, the intermediate (c) of the invention is used. The reaction solvent, reaction conditions, and the like are the same as in the case of using an amino group. At the reaction, a radical initiator such as iodine or AIBN may be used. A sulfide bond is formed between the bio-related substance and the intermediate of the invention by carrying out the reaction.

(Case of Reacting a Carboxyl Group of a Bio-related Substance with an Intermediate of the Invention)

In the case of the modification with a carboxyl group of a bio-related substance, the intermediate (c), (g), or (j) of the invention is used. The reaction solvent, reaction conditions, and the like are the same as in the case of using an amino group. At the reaction, a condensing agent such as DCC or EDC may be optionally used. A covalent bond is formed between the bio-related substance and the intermediate of the invention by carrying out the reaction, and a thioester bond is formed in the case of using (c) and an amide bond in the case of using (g) or (j).

(Case of Reacting an Aldehyde Group of a Bio-related Substance with an Intermediate of the Invention)

In the case of the modification with an aldehyde group of a bio-related substance, the intermediates (c), (g), (j), (xx2), and (xx3) of the invention are used. The reaction solvent, the reaction conditions, and the like are the same as in the case of using the amino group. When a Schiff base is formed, it may be subjected to a reduction treatment using a reducing agent such as sodium cyanoborohydride. By carrying out the reaction, a thioacetal bond is formed in the case of using (c), a secondary amino group in the case of using (g) or (j), an oxime in the case of using (xx2), and a hydrozone bond in the case of using (xx3).

Moreover, in the case that a bio-related substance does not have any of an amino group, a mercapto group, an unsaturated bond, a carboxyl group, and an aldehyde group, the substance can be modified by introducing a reactive group suitably into the bio-related substance and using an intermediate of the invention.

(Production of Intermediates)

The intermediates of the invention can be, for example, produced as follows. An alkyleneoxide is polymerized in an amount of 0 to 1000 mol to the primary hydroxyl group residue of 2,2-dimethyl-1,3-dioxolane-4-methanol and the terminal hydroxyl group is protected with a benzyl group or a t-Bu group. Thereafter, the cyclic acetal structure is deprotected under an acidic condition and an alkylene oxide is polymerized in an amount of 10 to 1000 mol to the newly formed two hydroxyl groups, followed by alkyl-etherification of the terminal ends. Then, the protective group such as the benzyl group or t-Bu group is deprotected and thereby, the compound of the general formula (p) can be obtained. When n is 0, the primary hydroxyl group residue of 2,2-dimethyl-1,3-dioxolane-4-methanol is protected with a benzyl group or t-Bu group and then an alkylene oxide is polymerized in an amount of 10 to 1000 mol to the newly formed two hydroxyl groups, followed by alkyl-etherification of the terminal ends. Then, the protective group such as the benzyl group or t-Bu group is deprotected and thereby, the compound of the general formula (p) can be obtained.

Alternatively, the compound (p) can be also produced by the following method. The primary hydroxyl group of 2,2-dimethyl-1,3-dioxolane-4-methanol is protected by a benzyl group or t-Bu group. Thereafter, the cyclic acetal structure is deprotected under an acidic condition and an alkylene oxide is polymerized in an amount of 10 to 1000 mol to the newly formed two hydroxyl groups, followed by alkyl-etherification of the terminal ends. Then, the protective group such as the benzyl group or t-Bu group is deprotected and thereby, the compound of the general formula (p) wherein n is 0 can be obtained. The compound may be also produced by polymerizing an alkylene oxide in an amount of 0 to 1000 mol to the newly formed hydroxyl group.

When n is 1 to 3, after coupling of 2,2-dimethyl-1,3-dioxolane-4-methanol with 2-benzyloxyethanol (n=1), diethylene glycol benzyl ether (n=2), or triethylene glycol benzyl ether (n=3), the cyclic acetal structure is deprotected under an acidic condition and an alkylene oxide is polymerized in an amount of 10 to 1000 mol to the newly formed two hydroxyl groups, followed by alkyl-etherification of the terminal ends. Then, the protective group such as the benzyl group or t-Bu group is deprotected and thereby, the compound of the general formula (p) can be obtained.

As above, a highly pure branched polyalkylene glycol derivative can be produced in high yields in an industrially suitable manner by using the alkylene oxide-addition polymerization reaction, without column purification.

Using the hydroxyl group of the compound (p) thus obtained, the intermediates of the invention can be produced by modifying hydroxy group into various reactive groups shown in the groups (I), (II) and (III). Furthermore, using the formed reactive groups, various bio-related substances can be reacted and modified to produce modified bio-related substances of the invention.

Moreover, the intermediate having each functional group of the groups (I), (II) and (III) can be reacted with a bio-related substance but in some cases, the intermediate can be further reacted with the other compound to produce other intermediate and the other intermediate can be then reacted with a bio-related substance. For example, using the intermediate having a functional group (g), (j), or (k) belonging to the group (II) as an starting material, the intermediate having (a), (e), or (f) of the group (I) can be synthesized.

The addition polymerization of an alkylene oxide to the primary hydroxyl group residue of 2,2-dimethyl-1,3-dioxolane-4-methanol can be carried out in the following manner. The addition polymerization of an oxyalkylene can be achieved in toluene or without solvent under an alkaline condition such as sodium, potassium, sodium hydride, potassium hydride, sodium methoxide, or potassium t-butoxide. In the case that n is 1 to 3, the step of the addition polymerization of alkylene oxide need not be carried out. The subsequent benzyl etherification can be carried out in the following manner.

1) It can be achieved by reacting benzyl chloride or benzyl bromide with 2,2-dimethyl-1,3-dioxolane-4-methanol or its alkylene oxide adduct in an aprotic solvent or without any solvent in the presence of an alkali catalyst such as sodium hydroxide or potassium hydroxide.

2) It can be achieved by converting the hydroxyl group of 2,2-dimethyl-1,3-dioxolane-4-methanol or its alkylene oxide adduct in an aprotic solvent or without any solvent using sodium, potassium, sodium hydride, potassium hydride, sodium methoxide, potassium methoxide, potassium t-butoxide, or the like into an alcoholate and reacting the alcoholate with benzyl chloride or benzyl bromide under a basic condition.

3) It can be achieved by activating the hydroxyl group of 2,2-dimethyl-1,3-dioxolane-4-methanol or its alkylene oxide adduct with methanesulfonyl chloride, p-toluenesulfonyl chloride, 2,2,2-trifluoroethanesulfonyl chloride, or the like in an aprotic solvent or without any solvent, followed by the reaction with an alcoholate of benzyl alcohol.

4) It can be achieved by activating the hydroxyl group of 2-benzyloxyethanol (n=1), diethylene glycol benzyl ether (n=2), or triethylene glycol benzyl ether (n=3) with methanesulfonyl chloride, p-toluenesulfonyl chloride, 2,2,2-trifluoroethanesulfonyl chloride, or the like in an aprotic solvent or without any solvent, followed by the reaction with an alcoholate of 2,2-dimethyl-1,3-dioxolane-4-methanol.

The deprotection of the cyclic acetal structure which follows the benzyl etherification is achieved by the reaction in an aqueous solution adjusted to pH 1 to 4 with an acid such as acetic acid, phosphoric acid, sulfuric acid, or hydrochloric acid, whereby a compound of the formula (9) can be produced.

The addition polymerization of an alkylene oxide to the compound of the following formula (9) having two hydroxyl groups newly formed by the deprotection of the cyclic acetal is not particularly limited but can be achieved via the following steps (C1) and (C2).

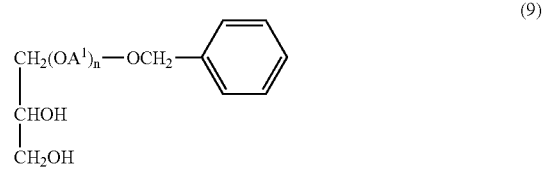

Step (C1): The alcoholation of the compound of the formula (9) is achieved by using sodium or potassium, preferably sodium as a catalyst in an catalyst amount of 5 to 50 mol %, followed by dissolution at 10 to 50° C.

Step (C2): An alkylene oxide addition polymerization is carried out at a reaction temperature of 50 to 130° C.

With regard to the catalyst amount in the step (C1), since the polymerization rate of the alkylene oxide decreases at less than 5 mol % and heat history increases to result in the formation of impurities such as a terminal vinyl ether compound, the use of the catalyst in an amount of 5 mol % or more is advantageous in the production of a high quality high-molecular-weight compound. When the catalyst amount exceeds 50 mol %, the viscosity of the reaction liquid increases or the liquid solidifies at the alcoholation reaction and thus there is a tendency that the stirring efficiency decreases and the alcoholation is not accelerated. Moreover, when the liquid solidifies, handling thereof tends to be difficult, which causes water absorption. When the alcoholate has absorbed water, an alkylene glycol compound derived from water is formed and is contained as an impurity undesirable in medical use.

When the temperature at the dissolution is higher than 50° C., a decomposition reaction may occur to form benzyl alcohol and glycerin. When benzyl alcohol is formed, it initiates addition polymerization with the alkylene oxide, whereby a low-molecular-weight impurity having a molecular weight 0.5 time the molecular weight of the target compound. When the low-molecular-weight impurity derived from benzyl alcohol is formed, a functional group is introduced via alkyl-etherification of the hydroxyl group and deprotection in the subsequent steps as in the case of the target compound, so that the impurity is converted into a low-molecular-weight impurity which is reactive with a bio-related substance. There is the possibility that such impurity may react with a bio-related substance and change the physical properties of the resulting preparation. Moreover, when glycerin is formed, it also initiates addition polymerization with the alkylene oxide to form a high-molecular-weight impurity having a molecular weight 1.5 times that of the target compound. Since the high-molecular-weight impurity does not have a benzyl group and its terminal hydroxyl group is only alkyl-etherified, no functional group is introduced. However, when the combination with a drug or the like is carried out while such impurity is contained, the resulting preparation becomes inhomogeneous and hence the quality tends to be varied. Also, the preparation is not suitable in a medical use where a highly pure product is required.

When the dissolution is carried out at a temperature lower than 10° C., like the case that the catalyst amount is more than 50 mol %, the viscosity of the reaction liquid increases or the liquid solidified at the alcoholation reaction, and handling thereof tends to be difficult, and water absorption is caused.

The reaction solvent is not particularly limited as far as it is an aprotic solvent such as toluene, benzene, xylene, acetonitrile, ethyl acetate, tetrahydrofuran, chloroform, methylene dichloride, dimethyl sulfoxide, dimethylformamide, or dimethylacetamide, but preferable is toluene or no solvent. The reaction time is preferably 1 to 24 hours. When the time is less than 1 hour, there is the possibility that the catalyst does not completely dissolved. When the time is longer than 24 hours, there is the possibility that the above decomposition reaction may occur.

With regard to the reaction temperature in the step (C2), when the temperature is lower than 50° C., the polymerization rate is low and heat history increases to result in a tendency to decrease the quality of the compound of the formula (5). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction liquid also increases, so that an aprotic solvent, preferably toluene may be optionally added.

As another production process in the step of alcoholation, the following step (C3) may be mentioned.

Step (C3): Sodium methoxide, potassium t-butoxide, or potassium methoxide, preferably sodium methoxide is added as an catalyst in an amount of 5 to 50 mol % and the reaction is carried out at 60 to 80° C. At that time, a pressure-reducing operation ay be conducted in order to facilitate the exchange reaction.

The catalyst amount is preferably 5 to 50 mol % for the reason entioned above. With regard to the reaction temperature, when the temperature is lower than 60° C., the conversion of the exchange reaction decreases and alcohols such as methanol remain, which leads to the formation of impurities having a molecular weight 0.5 time that of the target compound. When the temperature is higher than 80° C., a degradation reaction occurs. The alcoholation reaction requires elevation of the temperature and the reaction time is desirably 1 to 3 hours since the degradation reaction is apt to occur. When the time is shorter than 1 hour, there is the possibility that the conversion into the alcoholate decreases. When the time is longer than 3 hours, the decomposition may occur. The reaction solvent is not particularly limited as far as it is an aprotic solvent, but preferable is toluene or no solvent.

The subsequent alkyl-etherification of the terminal end may be achieved by either of the following (1) or (2):

(1) a process of converting the terminal end of the polyalkylene glycol chain into an alcoholate and reacting it with an alkyl halide;
(2) a process of activating the terminal hydroxyl group of the polyalkylene glycol chain with methanesulfonyl chloride, p-toluenesulfonyl chloride, 2,2,2-trifluoroethanesulfonyl chloride, or the like, followed by the reaction with an alcoholate of alkyl alcohol.

Preferable is the process (2) and the following will describe it in more detail.

The production process (2) comprises the following steps (B1), (B2), and (B3).

Step (B1): A step of adding a dehalogenating agent and a compound represented by the formula (6) to a compound represented by the formula (5) and reacting them at 20 to 60° C. to obtain a compound of the formula (7). At that time, each charged molar ratio satisfies the following relationship:

$$Vc \geq 3Va$$

$$Vb > Vc$$

Va: number of moles of the compound represented by the formula (5)
Vb: number of moles of the dehalogenating agent
Vc: number of moles of the compound represented by the formula (6).

More preferable is the case that each charged molar ratio satisfies the following relationship:

$$20Va \geq Vc \geq 3Va$$

$$4Vc > Vb > Vc.$$

When Vc is smaller than 3Va, the conversion decreases and thus some part of the hydroxyl groups in the oxyalkylene chain terminal ends remain unchanged. A functional group is introduced to the remaining hydroxyl group to form a polyfunctional impurity having a molecular weight the same as that of the target compound. When such polyfunctional impurity is present, it acts as a crosslinking agent at the combination with a bio-related substance to result in a tendency to decrease the purity of the resulting modified bio-related substance. When Vb is not larger than Vc, the conversion decreases owing to inefficient trapping of an acid which is produced as a by-product with the progress of the reaction, so that some part of the hydroxyl groups in the oxyalkylene chain terminal ends remain unchanged. Moreover, when Vc is larger than 20Va or Vb is not smaller than 4Vc, an excess of each reagent or compound may be contained to cause side reactions in the subsequent processes.

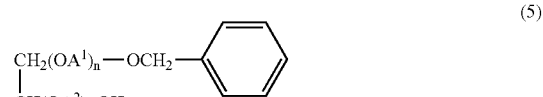
(5)

(6)

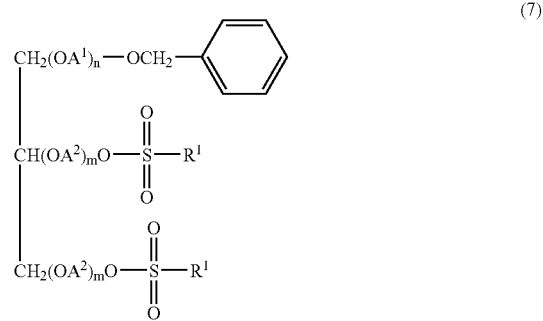
(7)

The dehalogenating agent to be used includes organic bases such as triethylamine, pyridine, and 4-dimethylaminopyridine, and inorganic bases such as sodium carbonate, sodium hydroxide, sodium hydrogen carbonate, sodium acetate, potassium carbonate, and potassium hydroxide. Preferable dehydrochlorinating agent is an organic base such as triethylamine, pyridine, or 4-dimethylaminopyridine.

In the compound of the formula (6) to be used, W is preferably Cl or Br, and $R^1$ is preferably a methyl group, a phenyl group, or a p-methylphenyl group. More suitably, methanesulfonyl chloride where W is Cl and $R^1$ is a methyl group is most preferable.

The solvent to be used at that time is not particularly limited as far as it is an aprotic solvent and preferably includes toluene, benzene, xylene, acetonitrile, ethyl acetate, tetrahydrofuran, chloroform, methylene dichloride, dimethyl sulfoxide, dimethylformamide, or dimethylacetamide, but more preferable is toluene which enables azeotropic removal of water in the system. The amount of the solvent to be used at the reaction is preferably 0.5 equivalent weight to 10 equivalent weight to the compound of the formula (5). In the case that the compound of the formula (5) has a large molecular weight, the viscosity of the reaction liquid increases and the conversion decreases, so that it is preferable to dilute the reaction liquid with the solvent.

The reaction temperature is not particularly limited but is preferably 60° C. or lower for the purpose of inhibiting side reactions and is preferably 20° C. or higher for the purpose of inhibiting increase of the viscosity of the reaction liquid. The reaction time is preferably 1 to 24 hours. When the time is less than 1 hour, there is the possibility that the conversion is low. When the time is longer than 24 hours, there is the possibility that a side reaction may occur.

At the reaction, the operation of removing water from the starting materials, such as azeotropic removal of water may be carried out prior to the reaction. Moreover, an antioxidant such as 2,6-di-tert-butyl-p-cresol may be added. Furthermore, a salt is formed with the progress of the reaction and the formation of the compound of the formula (7), but the reaction mixture may be used in the subsequent step as it is, or the salt may be removed by filtration, or after the filtration, the compound of the formula (7) may be purified by a purification means such as extraction, recrystallization, adsorption treatment, reprecipitation, column chromatography, or supercritical extraction.

Step (B2): A step of adding a compound represented by the formula (8) to the compound of the formula (7) and reacting them at 20 to 80° C. to obtain the compound of the formula (4). At that time, each charged molar ratio satisfies the following relationship:

$$Vd>Vc$$

Vd: number of moles of the compound represented by the formula (8).

More preferable is the case that the relationship:

$$10Vc>Vd>Vc$$

is satisfied.

$$R—OM \quad (8)$$

In the formula (8), R is as mentioned above and M is sodium or potassium, preferably sodium.

When Vd is not larger than Vc, the alkyl-etherification does not sufficiently proceed and a reactive group such as a mesylate group remains unchanged at the oxyalkylene chain terminal end. When a reactive group remains at the oxyalkylene chain terminal end, as mentioned above, a polyfunctional compound is formed and a serious side reaction is caused at the combination with a bio-related substance. Moreover, when Vd is not smaller than 10Vc, an excess of the alcoholate may be contained to cause side reactions in the subsequent process.

The solvent to be used in the reaction is not particularly limited as far as it is an aprotic solvent and is preferably toluene. The amount of the solvent to be used at the reaction is preferably an amount of 0.5 equivalent to 10 equivalent to the compound of the formula (7). In the case that the compound of the formula (7) has a large molecular weight, the viscosity of the reaction liquid increases, so that it is preferable to dilute the reaction liquid with the solvent.

The reaction temperature is not particularly limited but is preferably 80° C. or lower for the purpose of inhibiting side reactions and is preferably 20° C. or higher for the purpose of inhibiting increase of the viscosity of the reaction liquid. The reaction time is preferably 1 to 24 hours. When the time is less than 1 hour, there is the possibility that the conversion is low. When the time is longer than 24 hours, there is the possibility that a side reaction occurs. At the reaction, an operation of removing water from the starting materials, such as azeotropic removal of water may be carried out prior to the reaction.

Step (B3): A step of filtrating the reaction liquid or washing the reaction liquid with an aqueous inorganic salt solution having a concentration of 10 wt % or more.

In the step, the inorganic salt is not particularly limited but is preferably sodium chloride. When the concentration is less than 10 wt %, the target compound migrates into an aqueous layer to decrease the process yield remarkably. The operation of washing with water may be repeated several times. The step (B3) is carried out for removing starting materials excessively added and salts produced as by-products. The omission of the step may cause side reactions in the case that the steps (B1) to (B3) are again carried out in the next place. In the case that a debenzylation step is carried out as a next step, these impurities act as catalyst poisons and thus the conversion may be affected.

Moreover, in order to enhance the ratio of alkyl-etherification of the oxyalkylene chain terminal end, it is preferable to repeat the steps (B1) to (B3) again. When the ratio of alkyl-etherification of the oxyalkylene chain terminal end is low, as mentioned above, there is the possibility of forming a polyfunctional impurity.

The compound of the formula (4) thus obtained may be purified by a purification means such as extraction, recrystallization, adsorption treatment, reprecipitation, column chromatography, or supercritical extraction.

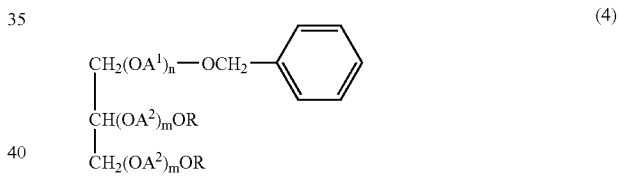

(4)

The production of the compound (p) by successive debenzylation is not particularly limited but it can be produced by hydrogenation of the following step (A) using a hydrogenative reduction catalyst and a hydrogen donor.

Step (A): A step of subjecting the compound represented by the formula (4) to a hydrogenative reduction reaction under the condition that the water content in the reaction system is 1% or less. When the water content in the reaction system is more than 1%, the decomposition reaction of the polyoxyalkylene chain occurs. Since polyalkylene glycol formed by the decomposition has a hydroxyl group, it is functionalized in the next step to form a reactive low-molecular-weight impurity. Such reactive low-molecular-weight impurity reacts with a bio-related substance as mentioned above and thus tends to change the properties of the resulting preparation.

The hydrogenative reduction catalyst is preferably palladium. The support is not particularly limited but is preferably alumina or carbon, more preferably carbon. The amount of palladium is preferably 1 to 20 wt % based on the compound of the formula (4). When the amount is less than 1 wt %, the conversion of deprotection decreases and thus there is the possibility that the ratio of functionalization in the next step decreases. Moreover, when the amount is more than 20 wt %, the decomposition reaction of the polyalkylene glycol chain may occur and there is the possibility that the above reactive low-molecular-weight compound is produced as a by-product. The reaction solvent is not particularly limited as far as the water content in the reaction system is less than 1%, but preferably includes methanol, ethanol, 2-propanol, and the like and more preferable is methanol. The hydrogen donor is not particularly limited but include hydrogen gas, cyclohexene, 2-propanol, and the like. The reaction temperature is preferably 40° C. or lower. When the temperature is higher than 40° C., the decomposition reaction of the polyalkylene glycol chain may occur and there is the possibility that the reactive low-molecular-weight compound is produced as a by-product. The reaction time is not particularly limited. When large amount of the catalyst is used, the reaction is completed within a short period of time. But, when the amount is small, a longer period of time is required. In general, the reaction time is preferably 1 to 5 hours. When the time is shorter than 1 hour, there is the possibility that the conversion is low. When it is longer than 5 hours, the decomposition reaction of the poly(alkylene glycol) may occur.

The resulting compound of the formula (p) may be purified by a purification means such as extraction, recrystallization, adsorption treatment, reprecipitation, column chromatography, or supercritical extraction.

The thus obtained compound is a polyalkylene glycol derivative represented by the following formula (p) and containing substantially no secondary hydroxyl group:

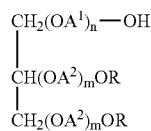
(p)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, and the groups represented by $OA^2$ are the same or different from each other in one molecule, n and m are each average number of moles of the oxyalkylene group added, n represents 0 to 1000, and m represents 10 to 1000.

Since the compound of the formula (p) contains no secondary hydroxyl group, the conversion of the subsequent functional group-introducing reaction is high and a highly pure polyalkylene glycol derivative can be obtained. In the case that a secondary hydroxyl group is present, the conversion of the subsequent functional group-introducing reaction is low and the purity of intermediate of the modified biorelated substance decreases, so that there may arise the problem of contamination of the drug or the like with an impurity.

The compound of the formula (p) of the invention satisfies the relationship:

$Hrd/Mp \times 1000000 \leq 3$ wherein Mp is a molecular weight corresponding to the peak top obtained from gel-permeation chromatography of the polyalkylene glycol derivative of the formula (p), and Hrd is a ratio of remaining hydroxyl group contained in the alkyl group R at the polyoxyalkylene chain terminal end in the 2- and 3-positions.

More preferably, it satisfies the relationship:

$Hrd/Mp \times 1000000 \leq 2$.

Mp means a weight-average molecular weight at the point of the maximum refractive index among peaks excluding the peaks caused by a developing solvent used in gel-permeation chromatography and false peaks derived from base line fluctuation caused by the column and apparatus used. In the invention, gel permeation chromatography is carried out using SHODEX GPC SYSTEM-11 as a GPC system and measurement was conducted under the following conditions: developing solvent: tetrahydrofuran; flow rate: 1 ml/min; column: SHODEX KF-801, KF-803, KF-804 (I.D. 8 mm×30 cm); column temperature: 40° C.; detector: RI X 8; sample amount: 1 mg/g, 100 µl.

The ratio Hrd of the remaining hydroxyl group contained in the alkyl group R is measured after mesylation of the compound of the formula (4) which is a precursor before deprotection. The following will illustrate the case that R is a methyl group.

5Ve g of toluene is added to Ve g of the compound of the formula (4), followed by removal of water azeotropically under normal pressure. After cooling to 40° C., 20 mol of triethylamine is added to 1 mol of the compound of the formula (4) and after thorough stirring, 6 mol of methanesulfonyl chloride is added thereto. At that time, it is desirable to add it dropwise after dilution with toluene or without dilution. Then, the reaction is carried out at 40° C. for 3 hours and triethylamine salt of methanesulfonic acid is removed by filtration. Then, 10Ve to 20Ve g of ethyl acetate is added to the filtrate and after cooling to room temperature, hexane is gradually added until crystals precipitate. The resulting crystals are collected by filtration and 10Ve to 20Ve g of ethyl acetate is again added to the crystals, followed by heating to dissolve them. After cooling to room temperature, hexane is gradually added until crystals precipitate. The crystals are collected by filtration and dried. A 20 mg portion of the resulting dried product is dissolved in deuterated chloroform and $^1H$ nuclear magnetic resonance spectrum is measured. Hrd is represented by the following relationship:

$Hrd = Mms/(Mms + Mme)$ wherein Mme is an integral value of peak of the methyl group of the oxyalkylene chain terminal end detected at 3.38 ppm and Mms is an integral value of peak of the mesyl group formed by mesylating the remaining hydroxyl group of the oxyalkylene chain terminal end, which is detected at 3.08 ppm, a TMS base peak being 0 ppm.

When R is a group other than a methyl group, Hrd can be determined by suitably identifying a peak position where the alkyl group is detected and applying a similar equation in consideration of the proton number.

When Hrd thus determined satisfies the following relationship:

$Hrd/Mp \times 1000000 > 3$, the case means that a large amount of impurities where hydroxyl groups remain at 2- and 3-positions of the polyoxyalkylene chain terminal end are contained. When such impurities are present, the hydroxyl group of the polyoxyalkylene chain terminal end are also functionalized in the subsequent step to form polyfunctional impurities. Such impurities may act as crosslinking agents at the combination with a biorelated substance as mentioned above to cause side reactions.

With regard to the compound of the formula (p) of the invention, polydispersity Mw/Mn in all the peaks from the starting point of elution to the end point of elution satisfies the relationship:

$Mw/Mn \leq 1.07$ at the measurement of gel permeation chromatography. More preferable is the case that the relationship:

$$Mw/Mn \leq 1.05$$

is satisfied.

In the case that Mw/Mn is larger than 1.07, it means the presence of a large amount of the above-mentioned high-molecular-weight impurities and low-molecular weight impurity and when the compound is combined with a bio-related substance, there is the possibility that the formation of by products increases to result in an insufficient purity. Moreover, when the purity is insufficient, the product may cause an adverse effect when used as an medical product.

The compound of the formula (p) of the invention satisfies the relationship:

$$M2/(M1+M2) \times 100 \leq 10$$

wherein M1 is an integral value of the methyl group detected at around 3.13 ppm, which is originated from the mesyl group derived from the hydroxyl group at the 1-position directly bonded to the glycerin skeleton in the case that n is 0 when the compound is reacted with methanesulfonyl chloride to obtain a mesylated compound and a nuclear magnetic resonance spectrum thereof is measured as a deuterated methanol solution, and M2 is an integral value of the methyl group detected at around 3.12 ppm, which is originated from the mesyl group derived from the hydroxyl group of the polyalkylene glycol chain. More preferably, the relationship:

$$M2/(M1+M2) \times 100 \leq 8$$

is satisfied.

The following will illustrate the calculation method of M1 and M2.

4Vf g of toluene is added to vf g of the compound of the formula (p), followed by removal of water azeotropically under normal pressure. After cooling to 40° C., 20 mol of triethylamine is added to 1 mol of the compound of the formula (p) and after thorough stirring, 6 mol of methanesulfonyl chloride is added thereto. At that time, it is desirable to add it dropwise after dilution with toluene or without dilution. Then, the reaction is carried out at 40° C. for 3 hours and triethylamine salt of methanesulfonyl chloride is removed by filtration. Thereafter, 10Vf to 20Vf g of ethyl acetate is added to the filtrate and after cooling to room temperature, hexane is gradually added until crystals precipitate. The resulting crystals are collected by filtration and 10Vf to 20Vf g of ethyl acetate is again added to the crystals, followed by heating to dissolve them. After cooling to room temperature, hexane is gradually added until crystals precipitate. The crystals are collected by filtration and dried. A 20 mg portion of the resulting dried product is dissolved in deuterated methanol and $^1$H nuclear magnetic resonance spectrum is measured. M1 is determined as an integral value of the methyl group detected at around 3.13 ppm, which is originated from the mesyl group derived from the hydroxyl group at the 1-position directly bonded to the glycerin skeleton in the case that n is 0, a TMS base peak being 0 ppm. Moreover, M2 is determined as an integral value of the methyl group detected at around 3.12 ppm, which is originated from the mesyl group derived from the polyalkylene glycol chain terminal end or polyalkylene glycol chain formed by the decomposition reaction.

In the case that the relationship:

$$M2/(M1+M2) \times 100 > 10$$

which is derived from M1 and M2 thus determined, is satisfied, the purity of the resulting modified bio-related substance tends to decrease because the substance is contaminated with a large amount of the impurities shown below.

That is, the case means that a large amount of impurities having a hydroxyl group at the polyoxyalkylene chain terminal end, which are originated from the impurities:

(A): an impurity having a hydroxyl group and a molecular weight 0.5 time that of the compound (p), which is formed by decomposition of the compound of the formula (9) at the alcoholation, addition polymerization of an alkylene oxide to the resulting benzyl alcohol, and deprotection of benzyl group in the subsequent step;

(B): an impurity having a remaining hydroxyl group at 2- or 3-position and a molecular weight the same as that of the compound (p), which is formed at the alkyl-etherification of the compound of the formula (5);

(C): an impurity having a hydroxyl group and a low molecular weight, which is formed by decomposition of the polyoxyalkylene chain at the debenzylation of the compound of the formula (4); and the like, are present.

The debenzylation reaction of the invention is widely applicable to other derivatives.

More specifically, it is a process for producing a polyalkylene glycol derivative of the formula (11), comprising the following step (AA):

Step (AA): a step of subjecting a compound represented by the formula (10) to a hydrogenative reduction reaction under the condition that the water content in the reaction system is 1% or less:

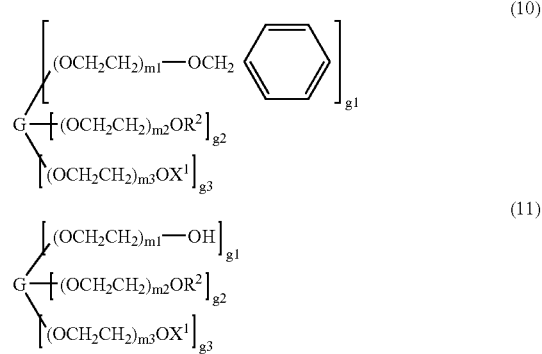

wherein G is a residual group of a compound having 2 to 4 hydroxyl groups; $R^2$ is a hydrocarbon group having 1 to 4 carbon atoms; m1, m2, and m3 represent each average number of moles of an oxyethylene group added and satisfy the following relationship:

$$0 \leq m1 \leq 1000, 0 \leq m2 \leq 1000, 0 \leq m3 \leq 1000, 10 \leq m1+m2+m3 \leq 1000;$$

$X^1$ is an amino group, a carboxyl group, or a protected group thereof; and g1, g2, and g3 represent each an integer and satisfy the following relational equations:

$$1 \leq g1 \leq 3, 0 \leq g2, 0 \leq g3, 2 \leq g1+g2+g3 \leq 4.$$

More specific residual group of a compound having 2 to 4 hydroxyl groups in G includes ethylene glycol, glycerin, pentaerythritol, diglycerin, and the like, and more preferable is ethylene glycol or glycerin.

More specific $R^2$ includes a methyl group, an ethyl group, a propyl group, an isopropyl group, a t-butyl group, and the like, and preferable is a methyl group.

With regard to m1, m2, and m3, they are not particularly limited as far as the relationships:

$$0 \leq m1 \leq 1000,\ 0 \leq m2 \leq 1000,\ 0 \leq m3 \leq 1000,\ 10 \leq m1+m2+m3 \leq 1000$$

are satisfied, but preferable is the case of $20 \leq m1+m2+m3 \leq 1000$, more preferably is the case of $40 \leq m1+m2+m3 \leq 1000$, and most preferable is the case of $100 \leq m1+m2+m3 \leq 1000$.

Specific $X^1$ includes an amino group, a Boc amino group, an Fmoc amino group, a carboxyl group, and the like, and more preferable is a Boc amino group, wherein Boc means a t-butoxycarbonyl group and Fmoc means a 9-fluorenyl-methoxycarbonyl group.

The water content in the reaction system, catalyst amount, reaction time, solvent, and the like are the same as those in the aforementioned step (A). The hydrogenative reduction reaction can be carried out using a hydrogenative reduction catalyst. The hydrogenative reduction catalyst is preferably palladium.

The alkyl-etherification of the invention is widely applicable to other derivatives.

More specifically, it is a process for producing a polyalkylene glycol derivative represented by the formula (16), wherein the following steps (BB1) to (BB3) are carried out.

Step (BB1): A step of adding a dehalogenating agent and a compound represented by the formula (14) to a compound represented by the formula (12) and reacting them at 20 to 60° C. to obtain a compound of the formula (13). At that time, each charged molar ratio satisfies the following relationship:

$$Vj \geq 1.5 \times Vh \times g5$$

$$Vi > Vj$$

Vh: number of moles of the compound represented by the formula (12)

Vi: number of moles of the dehalogenating agent

Vj: number of moles of the compound represented by the formula (14).

Step (BB2): A step of adding a compound represented by the formula (15) to a compound of the formula (13) and reacting them at 20 to 80° C. to obtain a compound of the formula (16). At that time, each charged molar ratio satisfies the following relationship:

$$Vk > Vj$$

Vk: number of moles of the compound represented by the formula (15):

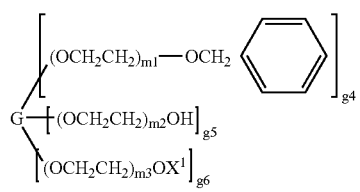

(12)

wherein G, m1, m2, m3, and $X^1$ are the same as above, and g4, g5, and g6 represent each an integer and satisfy the following relational equations:

$$0 \leq g4,\ 1 \leq g5 \leq 3,\ 0 \leq g6,\ 2 \leq g4+g5+g6 \leq 4.$$

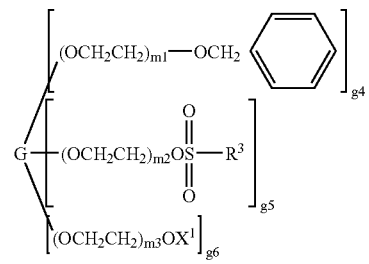

(13)

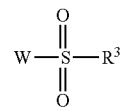

(14)

wherein G, m1, m2, m3, and $X^1$ are the same as above, W is a halogen atom selected from Cl, Br and I, and $R^3$ is a hydrocarbon group having 1 to 10 carbon atoms.

$$R^2\text{---OM} \qquad (15)$$

wherein $R^2$ is the same as above and M is potassium or sodium.

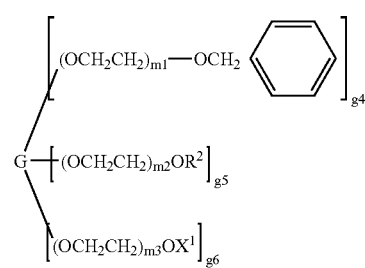

(16)

wherein G, $R^2$, m1, m2, m3, and X are the same as above.

Step (BB3): A step of filtrating the reaction liquid or washing the reaction liquid with an aqueous inorganic salt solution having a concentration of 10 wt % or more.

In the compound of the formula (14), W is preferably Cl or Br, and $R^3$ is preferably a methyl group, a phenyl group, or a p-methylphenyl group, and most preferable is methanesulfonyl chloride where W is Cl and $R^3$ is a methyl group.

The inorganic salt is not particularly limited but is preferably sodium chloride.

Moreover, for the aforementioned reasons, in order to enhance the ratio of alkyl-etherification of the oxyethylene chain terminal end, it is preferable to repeat again the steps (BB1) to (BB3).

The water content in the reaction system, catalyst amount, reaction time, solvent, and the like are the same as the aforementioned steps (B1) to (B3).

The following shows the reaction pathways to the compound (p).

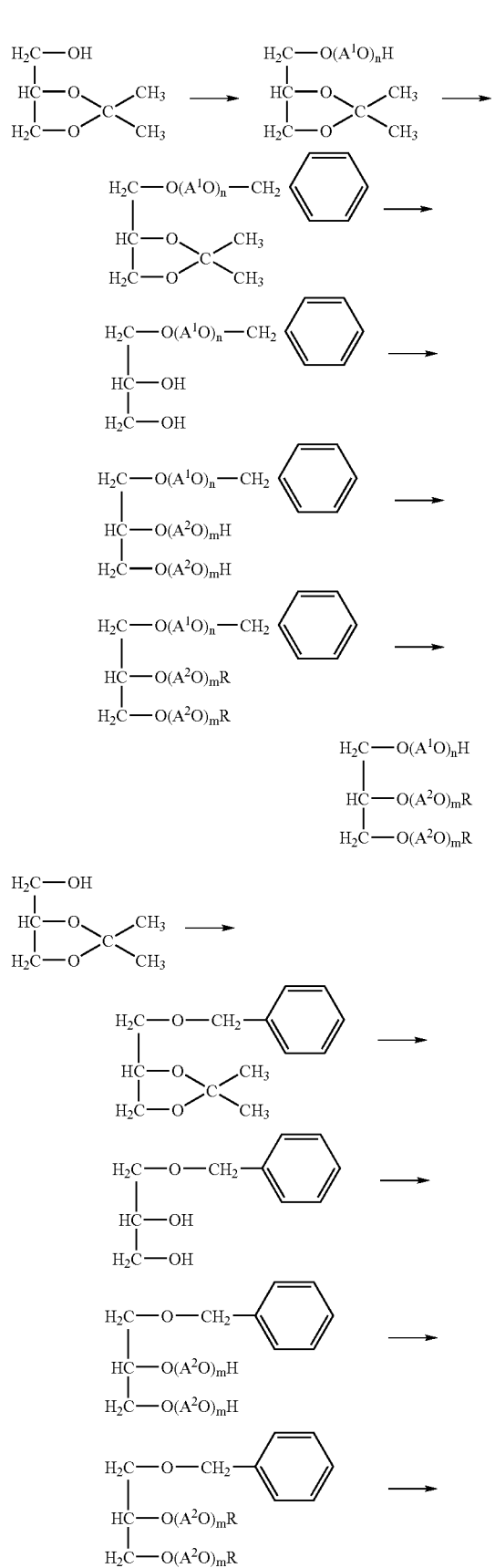

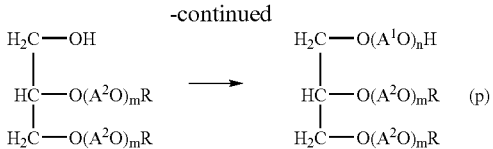

The following will describe the introduction of a reactive group into the hydroxyl group of the compound (p) formed by the debenzylation reaction.

(Process for Producing (b), (d), (h), and (i))

By reacting the compound (p) with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and any one of the compounds represented by the following general formulae (b1), (d1), (h1), and (i1) in an aprotic solvent such as toluene, benzene, xylene, acetonitrile, ethyl acetate, diethyl ether, t-butyl methyl ether, tetrahydrofuran, chloroform, methylene dichloride, dimethyl sulfoxide, dimethylformamide, or dimethylacetamide or without any solvent, (b), (d), (h), and (i) can be introduced, respectively. Moreover, the above organic base or inorganic base need not be used. The ratio of the organic base or inorganic base to be used is not particularly limited but is preferably equimolar or more to the compound (p). Furthermore, an organic base may be used as a solvent. W in (b1) or (d1) is a halogen atom selected from Cl, Br and I, and is preferably Cl. The ratio of the compounds represented by the general formulae (b1), (d1), (h1), and (i1) to be used is not particularly limited but is preferably equimolar or more, more preferably equimolar to 50 molar to the compound (p). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, column chromatography, or supercritical extraction.

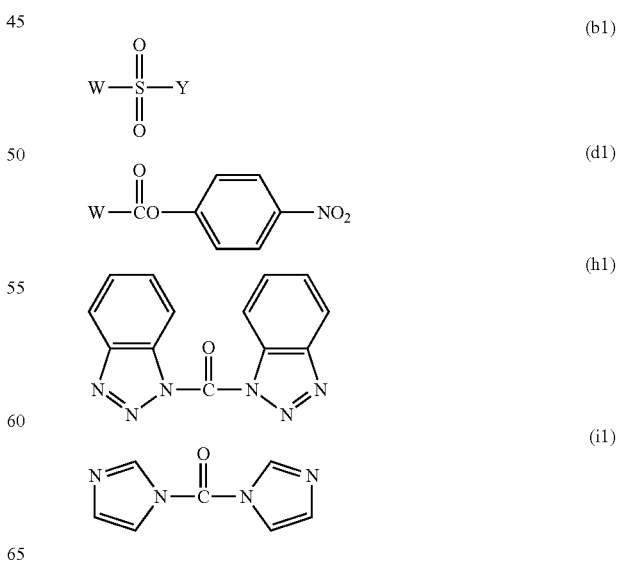

wherein W is a halogen atom selected from Cl, Br and I.

(Process for Producing (a) and (k))

The succinimide compound (a) can be obtained by reacting the compound (p) with a dicarboxylic acid anhydride such as succinic anhydride or glutaric anhydride to obtain a carboxyl compound (k), followed by condensation with N-hydroxysuccinimide in the presence of a condensing agent such as DCC or EDC. The reaction of the compound (p) with a dicarboxylic acid anhydride is carried out in the aforementioned aprotic solvent or without any solvent. The ratio of the dicarboxylic acid anhydride to be used is not particularly limited but is preferably equimolar or more, more preferably equimolar to 5 molar to the compound (p). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50 wt %, more preferably 0.5 to 20 wt %. The carboxyl compound (k) thus formed may be purified by the aforementioned purification means or may be used as it is in the next condensation reaction.

The subsequent condensation reaction is also carried out in the aforementioned aprotic solvent or without any solvent. The condensing agent is not particularly limited but is preferably DCC.

The ratio of DCC to be used is preferably equimolar or more, more preferably equimolar to 5 molar to the compound (p). The ratio of N-hydroxysuccinimide to be used is preferably equimolar or more, more preferably equimolar to 5 molar to the compound (p). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

The compound (a) can be obtained also by the flowing method. It can be obtained by reacting the compound (p) with N,N'-disuccinimidyl carbonate. The reaction of the compound (p) with N,N'-disuccinimidyl carbonate is carried out in the aforementioned aprotic solvent or without any solvent. The ratio of N,N'-disuccinimidyl carbonate to be used is not particularly limited but is preferably equimolar or more, more preferably equimolar to 20 molar to the compound (p). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50 wt %, more preferably 0.5 to 20 wt %. The compound (a) thus formed may be purified by the aforementioned purification means.

(Process for Producing (g) and (j))

The amine compound (g) can be obtained by reacting the compound (p) to acrylonitrile or the like using an inorganic base such as sodium hydroxide or potassium hydroxide in a solvent such as water and acetonitrile to obtain a nitrile compound and then subjecting it to hydrogenation of the nitrile group in the presence of a nickel or palladium catalyst in an autoclave. The ratio of the inorganic base to be used for obtaining the nitrile compound is not particularly limited but is preferably 0.01 to 50 wt % to the compound (p). The ratio of acrylonitrile or the like to be used is not particularly limited but is preferably 0.5 to 5 equivalent weight, more preferably 1 to 4 equivalent weight to the weight of the compound (p). Moreover, acrylonitrile may be used as a solvent. The reaction temperature is preferably −50 to 100° C., more preferably −20 to 60° C. The reaction time is preferably 10 minutes to 48 hours, more preferably 30 minutes to 24 hours. The reaction solvent in the subsequent hydrogenation reaction is not particularly limited as far as it does not participate in the reaction, but is preferably toluene. The ratio of the nickel or palladium catalyst to be used is not particularly limited but is 0.05 to 30 wt %, preferably 0.5 to 20 wt % to the nitrile compound. The reaction temperature is preferably 20 to 200° C., more preferably 50 to 150° C. The reaction time is preferably 10 minutes to 48 hours, more preferably 30 minutes to 24 hours. The hydrogen pressure is preferably 2 to 10 MPa, more preferably 3 to 8 MPa. Moreover, in order to prevent dimerization, ammonia may be added to the reaction system. In the case of adding ammonia, the ammonia pressure is not particularly limited but is 0.1 to 10 MPa, more preferably 0.3 to 2 MPa. The compound formed may be purified by the aforementioned purification means.

The above amine compound (g) or (j) can be also obtained by reacting (b) with aqueous ammonia. The reaction is carried out in aqueous ammonia and the concentration of ammonia is not particularly limited but is preferably in the range of 10 to 40%. The ratio of aqueous ammonia to be used is preferably 1 to 300 times the weight of (b). The reaction temperature is preferably 0 to 100° C., more preferably 20 to 80° C. The reaction time is preferably 10 minutes to 72 hours, more preferably 1 hour to 36 hours. Alternatively, the amine compound (g) or (j) can be also obtained by reacting (b) with ammonia in an autoclave. The reaction solvent is not particularly limited but preferably includes methanol and ethanol. The amount of ammonia is preferably 10 to 300 wt %, more preferably 20 to 200 wt %. The reaction temperature is preferably 50 to 200° C., more preferably 80 to 150° C. The reaction time is preferably 10 minutes to 24 hours, more preferably 30 minutes to 12 hours. The compound formed may be purified by the aforementioned purification means.

(Process for Producing (e))

Furthermore, the maleimide compound (e) can be obtained by reacting the resulting amine (g) with maleic anhydride in the aforementioned aprotic solvent or without any solvent to obtain an maleamide compound and then subjecting it to a ring closure reaction using acetic anhydride or sodium acetate. The ratio of maleic anhydride to be used in the maleamidation reaction is not particularly limited but is preferably equimolar or more, more preferably equimolar to 5 molar to the compound (p). The reaction temperature is preferably 0 to 200° C., more preferably 20 to 120° C. The reaction time is preferably 10 minutes to 48 hours, more preferably 30 minutes to 12 hours. The maleamide compound formed may be purified by the aforementioned purification means or may be used as it is in the next ring closure reaction.

The reaction solvent in the subsequent ring closure reaction is not particularly limited but is preferably aprotic solvent or acetic anhydride. The ratio of sodium acetate to be used is not particularly limited but is preferably equimolar or more, more preferably equimolar to 50 molar to the maleamide compound. The reaction temperature is preferably 0 to 200° C., more preferably 20 to 150° C. The reaction time is preferably 10 minutes to 48 hours, more preferably 30 minutes to 12 hours. The compound formed may be purified by the aforementioned purification means.

The above maleimide compound can be also obtained by reacting the compound of the following formula (e1) with the aforementioned amine (g) or (j). The reaction is carried out in the aforementioned aprotic solvent or without any solvent and the compound (e1) is added in an amount of equimolar or more to the amine (g) or (j). The ratio of the compound (e1) to be used is preferably equimolar or more, more preferably equimolar to 5 molar to the amine (g) or (j). The reaction temperature is preferably 0 to 200° C., more preferably 20 to 80° C. The reaction time is preferably 10 minutes to 48 hours, more preferably 30 minutes to 12 hours. During the reaction, light shielding may be conducted. The compound formed may be purified by the aforementioned purification means.

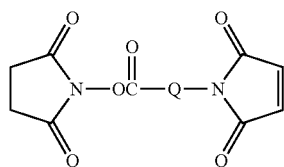
(e1)

wherein Q represents a hydrocarbon group having 1 to 7 carbon atoms.

(Process for Producing (f))

The aldehyde compound (f) can be obtained by reacting the compound (b) with an acetal compound (f1) to obtain an acetal compound and then subjecting it to hydrolysis under an acidic condition. The compound (b) is produced as mentioned above. The acetalization reaction can be achieved by reacting the compound (b) with an equimolar or more amount, preferably an equimolar to 50 molar amount of the compound (f1) in the aforementioned aprotic solvent or without any solvent. The compound (f1) can be prepared from the corresponding alcohol using sodium, potassium, sodium hydride, sodium methoxide, potassium t-butoxide, or the like. The reaction temperature is preferably 0 to 300° C., more preferably 20 to 150° C. The reaction time is preferably 10 minutes to 48 hours, more preferably 30 minutes to 24 hours.

In the case of using the compound (f 2), an acetal compound can be obtained by converting the hydroxyl group of the compound (p) into an alcoholate by the aforementioned method and then reacting it with an equimolar or more amount, preferably an equimolar to 100 molar amount of the compound (f2) in the aforementioned aprotic solvent or without any solvent. The reaction temperature is preferably 0 to 300° C., more preferably 20 to 150° C. The reaction time is preferably 10 minutes to 48 hours, more preferably 30 minutes to 24 hours.

In the case of using the compound (f3), an acetal compound can be obtained by reacting the compound (f3) with the compound (a), (b), (d), (h), (i), or (k). The compound (a), (b), (d), (h), (i), or (k) is produced as mentioned above. In the reaction with the compound (f3), the solvent is not particularly limited but the reaction is preferably carried out in the aforementioned aprotic solvent. The charging ratio of the compound (f3) is preferably equimolar or more, more preferably equimolar to 10 molar to the compound (a), (b), (d), (h), (i), or (k). The reaction temperature is preferably −30 to 200° C., more preferably 0 to 150° C. The reaction time is preferably 10 minutes to 48 hours, more preferably 30 minutes to 24 hours. In the case of using the compound (k), a condensing agent such as DCC or EDC may be optionally used. Any acetalization reaction may be carried out under light shielding. The acetal compound thus obtained may be purified by the aforementioned purification means or may be used as it is in the next aldehyde-formation reaction.

The aldehyde compound can be produced by hydrolyzing the acetal compound in a 0.1 to 50% aqueous solution which is adjusted to pH 1 to 4 with an acid such as acetic acid, phosphoric acid, sulfuric acid, or hydrochloric acid. The reaction temperature is preferably −20 to 100° C., more preferably 0 to 80° C. The reaction time is preferably 10 minutes to 24 hours, more preferably 30 minutes to 10 hours. The reaction may be carried out under light shielding. The compound formed may be purified by the aforementioned purification means.

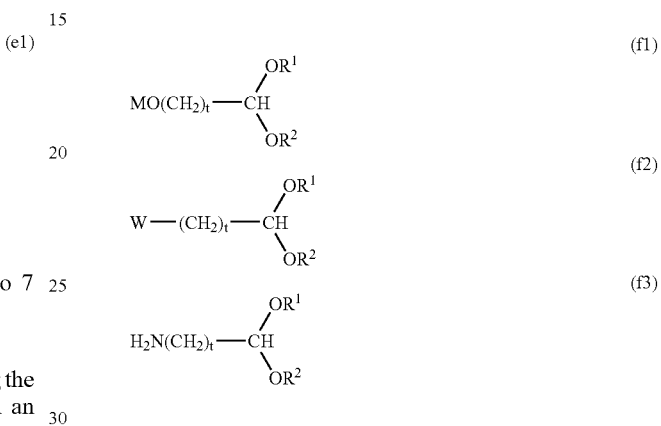

wherein $R^1$ and $R^2$ are each a hydrocarbon group having 1 to 3 carbon atoms and may be the same or different from each other, and they may together form a ring; M is sodium or potassium; W is a halogen atom selected from Cl, Br, and I; and t is an integer of 1 to 5.

(Process for Producing (c))

The mercapto compound (c) can be obtained by reacting the compound (b) with a thiol-forming agent such as thiourea. The compound (b) is produced as mentioned above. The thio-formation reaction is carried out in a solvent such as water, an alcohol, or acetonitrile or without any solvent. The ratio of thiourea to be used is equimolar or more, more preferably equimolar to 50 molar to the compound (b). The reaction temperature is preferably 0 to 300° C., more preferably 20 to 150° C. The reaction time is preferably 10 minutes to 48 hours, more preferably 30 minutes to 24 hours. After the reaction, the mercapto compound can be obtained by subjecting the resulting thiazolium salt to alkali hydrolysis. The compound formed may be purified by the aforementioned purification means.

Moreover, the above mercapto compound can be also obtained by reacting the compound (b) with the following compound (c1), followed by decomposition with a primary amine. The reaction of the compound (b) with the compound (c1) is carried out in the aforementioned aprotic solvent or without any solvent. The ratio of the compound (c1) to be used is equimolar or more, more preferably equimolar to 50 molar to the compound (b). The reaction temperature is preferably 0 to 300° C., more preferably 20 to 80° C. The reaction time is preferably 10 minutes to 48 hours, more preferably 30 minutes to 24 hours. The subsequent alkali decomposition with a primary amine is carried out in the aforementioned aprotic solvent or without any solvent. The primary amine to be used is not particularly limited but preferably includes ammonia, methylamine, ethylamine, propylamine, butylamine, pentylamine, hexylamine, cyclohexylamine, ethanolamine, propanolamine, and butanolamine. Naturally, the primary amine may be used as a solvent. The compound formed may be purified by the aforementioned purification means.

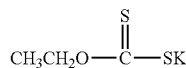
(c1)

(Production Method of (xx1))

The haloacetyl compound (xx1) can be, for example, produced by the following method. It can be obtained by reacting the compound (p), (g) or (j) with a compound represented by the following general formula (xx1a) and an organic bases such as triethylamine, pyridine, and 4-dimethylaminopyridine or an inorganic base such as sodium carbonate, sodium hydroxide, sodium hydrogen carbonate, sodium acetate, potassium carbonate, or potassium hydroxide in an aprotic solvent such as toluene, benzene, xylene, acetonitrile, ethyl acetate, diethyl ether, t-butyl methyl ether, tetrahydrofuran, chloroform, methylene dichloride, dimethyl sulfoxide, dimethylformamide, or dimethylacetamide or without any solvent. The ratio of the organic base or inorganic base to be used is not particularly limited but is preferably equimolar or more to the compound (p), (g) or (j). Moreover, an organic base may be used as a solvent. The organic or inorganic base is optionally used. $W^1$ in (xx1a) is a halogen atom selected from Cl, Br and I, and is preferably I. Furthermore, $W^1$'s may be the same or different from each other. The ratio of the compound represented by the formula (xx1a) to be used is not particularly limited but is preferably equimolar or more, more preferably equimolar to 50 molar to the compound (p), (g) or (j). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, column chromatography, or supercritical extraction.

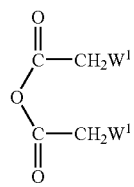
(xx1a)

(Production Method of (xx2))

The compound (xx2) can be, for example, produced by the following method. The hydrazine derivative (xx2) can be obtained by condensing the compound (k) with the following compound (xx2a) in the presence of a condensing agent such as DCC, EDC, or BOP [(benzotriazolyloxy) tris(dimethylamino)phosphonium hexafluorophosphate]. The reaction of the compound (p) with (xx2a) is carried out in the aforementioned aprotic solvent or without any solvent. The ratio of the (xx2a) to be used is not particularly limited but is preferably equimolar or more, more preferably equimolar to 5 molar to the compound (p). The condensing agent is not particularly limited but is preferably DCC, EDC, or BOP. The ratio of the condensing agent to be used is preferably equimolar or more, more preferably equimolar to 5 molar to the compound (p). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

(xx2a)

wherein Boc represents a t-butoxycarbonyl group.

The subsequent deprotection of the Boc group can be achieved by a known method. The compound (xx2) synthesized may be purified by the aforementioned purification means.

(Production Method of (xx3))

The compound (xx3) can be, for example, produced by the following method. The hydroxylamine derivative (xx3) can be obtained by condensing the compound (p), (g), or (j) with the following compound (xx3a) in the presence of a condensing agent such as DCC, EDC, or BOP. The reaction of the compound (p) with (xx3a) is carried out in the aforementioned aprotic solvent or without any solvent. The ratio of the (xx3a) to be used is not particularly limited but is preferably equimolar or more, more preferably equimolar to 5 molar to the compound (p). The condensing agent is not particularly limited but is preferably DCC, EDC, or BOP. The ratio of the condensing agent to be used is preferably equimolar or more, more preferably equimolar to 5 molar to the compound (p). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

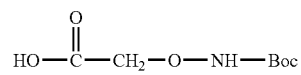
(xx3a)

The subsequent deprotection of the Boc group can be achieved by a known method. The compound (xx3) synthesized may be purified by the aforementioned purification means.

According to the invention, a bio-related substance modified with a branched poly(alkylene glycol)oxy group can be obtained. The bio-related substance is formed by ether bonds only except for the linker part with the poly(alkylene glycol)oxy group, so that a high stability can be expected with no decomposition to a single chain. Therefore, by modifying a bio-related substance with a branched polyalkylene glycol, a bio-related substance exhibiting an improved behavior in a body can be provided. The intermediate of the bio-related substance of the invention is a novel compound having a reactive group, which can be combined with a bio-related substance, at the primary carbon at the 1-position of the glycerin skeleton and having polyalkylene glycol chains at the 2- and 3-positions.

EXAMPLES

The following will describe the invention more specifically based on Examples. In this regard, $^1$H-NMR and GPC were employed for analyzing and identifying the compounds in Examples.

Method for $^1$H-NMR Analysis:

At $^1$H-NMR analysis, JNM-ECP400 manufactured by Nippon Denshi Datum K.K. The integral values in NMR data are theoretical values.

Method for GPC Analysis:

At GPC analysis, SHODEX GPC SYSTEM-11 was employed as a GPC system and measurement was carried out under the following conditions:

developing solvent: tetrahydrofuran; flow rate: 1 ml/min; column: SHODEX KF-801, KF-803, KF-804 (I.D. 8 mm×30 cm); column temperature: 40° C.; detector: RI X 8; sample amount: 1 mg/g, 100 µl.

In GPC data, analysis values at main peaks which are obtained by cutting elution curves perpendicular to base lines at inflection points to remove high-molecular-weight impurities and low-molecular-weight impurities and analysis values over whole peaks from start points of elution to end points of elution.

Mn represents a number average molecular weight, Mw a weight average molecular weight, and Mp a peak top molecular weight.

For the measurement of water content, a Karl Fisher's moisture meter (7S8/3-20 type manufactured by Metrome-Shibata) was employed and "HYDRANAL-composite 2" manufactured by Sigma Aldrich was employed as a Karl Fisher's reagent.

Example 1

Synthesis of Compound (p) (Case of R=Methyl Group, $A^1O$, $A^2O$=Oxyethylene Group, n=0, and Molecular Weight=About 10000)

Example 1-1

To a 1000 ml round-bottom flask fitted with a thermometer, a nitrogen-introducing tube, and a stirrer were added 132.2 g (1.0 mol) of 2,2-dimethyl-1,3-dioxolane-4-methanol, 231.4 g (1.2 mol) of a 28% methanol solution of sodium methoxide, and 500 ml of toluene. With introduction of nitrogen thereinto, the toluene was refluxed under reduced pressure for 1 hour to remove the methanol by distillation. With maintaining the solution at 80° C., 126.6 g (1.0 mol) of benzyl chloride was added dropwise over a period of 2 hours using a dropping funnel, followed by further 2 hours of reaction. The solvent was removed from the reaction liquid and the residue was purified by distillation (b.p. 93-95° C./266 Pa) to obtain 4-(benzyloxymethyl)-2,2-dimethyl-1,3-dioxolane.

$^1$H-NMR (CDCl$_3$, internal standard: TMS) δ(ppm): 1.36, 1.42 (3H, 3H, s, C(CH$_3$)$_2$), 3.45-3.57 (2H, m, CH$_2$O—C(CH$_3$)$_2$), 3.73-3.76 (1H, m, C$\underline{H}$O—C(CH$_3$)$_2$), 4.03-4.07, 4.28-4.32 (2H, m, CH$_2$O—CH$_2$Ph), 4.57 (2H, q, —CH$_2$Ph), 7.15-7.40 (5H, m, —CH$_2$P$\underline{h}$) (Ph represents a phenyl group)

Example 1-2

Into a 1 L beaker were weighed 222 g (1.0 mol) of 4-(benzyloxymethyl)-2,2-dimethyl-1,3-dioxolane purified in Example 1-1, 250 ml of ethanol, and 400 ml of distilled water, and the whole was adjusted to pH 2 with phosphoric acid. With introduction of nitrogen thereinto, the solution was heated to 70° C. After 1.5 hours of reaction, the solution was adjusted to pH 7.0 with sodium hydroxide, the resulting salts were adsorbed onto an adsorbent "KYOWAAD 1000" (manufactured by Kyowa Chemical Industry Co., Ltd.), and the solvent was removed to obtain 3-benzyloxy-1,2-propanediol.

$^1$H-NMR (CDCl$_3$, internal standard: TMS) δ(ppm): 3.50-3.71 (4H, m, CH$_2$OH, CH$_2$O—CH$_2$Ph), 3.86-3.91 (1H, m, C$\underline{H}$OH), 4.54 (2H, m, —C$\underline{H}_2$Ph), 7.27-7.38 (5H, m, —CH$_2$P$\underline{h}$).

Example 1-3

To a 300 ml round-bottom flask fitted with a thermometer, a nitrogen-introducing tube, and a stirrer were added 27.3 g (0.15 mol) of 3-benzyloxy-1,2-propanediol, 127 g of dry toluene, and 0.9 g (39 mmol: 26 mol %) of sodium. With introduction of nitrogen thereinto, the whole was stirred at room temperature until sodium dissolved. The solution was charged into a 5 L autoclave and the atmosphere was replaced by nitrogen, followed by heating to 100° C. Then, 1473 g (33.5 mol) of ethylene oxide was added thereto at 100 to 150° C. under a pressure of 1 MPa or lower, followed by continuation of the reaction for another 1 hour. Unreacted ethylene oxide gas was removed under reduced pressure, then the whole was cooled to 60° C. and adjusted to pH 7.5 with 85% aqueous phosphoric acid solution to obtain the following compound (p1).

$^1$H-NMR (CDCl$_3$, internal standard: TMS) δ(ppm): 3.40-3.80 (901H, m, —CH$_2$O(CH$_2$CH$_2$O)$_m$H, C$\underline{H}$O(CH$_2$CH$_2$O)$_m$H, CH$_2$OCH$_2$Ph), 4.54 (2H, s, —CH$_2$Ph), 7.27-7.38 (5H, m, —CH$_2$P$\underline{h}$). GPC analysis: <main peak> number average molecular weight (Mn): 9978, weight average molecular weight (Mw): 10171, polydispersity (Mw/Mn): 1.019, peak top molecular weight (Mp): 10044; <whole peak> number average molecular weight (Mn): 9865, weight average molecular weight (Mw): 10114, polydispersity (Mw/Mn): 1.025, peak top molecular weight (Mp): 10044.

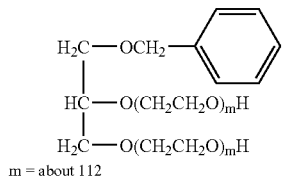

(p1)

m = about 112

Example 1-4

Into a 500 ml round-bottom flask fitted with a thermometer, a nitrogen-introducing tube, a stirrer, a Dean-stark tube, and a condenser tube were added 100 g (10 mmol) of the above compound (p1) and 320 g of toluene, and the whole was heated under reflux to effect azeotropic removal of water. After cooling to room temperature, 10.12 g (100 mmol) of triethylamine and 6.87 g (60 mmol) of methanesulfonyl chloride were added thereto, followed by 6 hours of reaction at 40° C. The reaction liquid was filtered and the filtrate was transferred into a 500 ml round-bottom flask fitted with a thermometer, a nitrogen-introducing tube, a stirrer, and a condenser tube. Then, 19.3 g (100 mmol) of 28% methanol solution of sodium methoxide was added thereto, followed by 6 hours of reaction at 70° C. Subsequently, 27 g of an adsorbent "KYOWAAD 700" (manufactured by Kyowa Chemical Industry Co., Ltd.) was added to the reaction liquid and the whole was further stirred at 70° C. for 1 hour to adsorb excessive sodium methoxide. After filtration of the reaction liquid, the filtrate was charged into a 1 L beaker and crystallization was carried out by adding 300 g of ethyl acetate and 350 g of hexane. The precipitated crystals were collected into a 1 L beaker by filtration and dissolved under heating at 40° C. with adding 400 g of ethyl acetate. Thereafter, 300 g of hexane was added and crystallization was again carried out. The precipitated crystals were collected by filtration and dried to obtain the following compound (p2).

$^1$H-NMR (CDCl$_3$, internal standard: TMS) δ(ppm): 3.38 (6H, s, —CH$_3$), 3.40-3.80 (901H, m, —CH$_2$O(CH$_2$CH$_2$O)$_m$CH$_3$, CHO(CH$_2$CH$_2$O)$_m$CH$_3$, CH$_2$OCH$_2$Ph), 4.54 (2H, s, —CH$_2$Ph), 7.27-7.38 (5H, m, —CH$_2$Ph). GPC analysis: <main peak> number average molecular weight (Mn): 10320, weight average molecular weight (Mw): 10551, polydispersity (Mw/Mn): 1.022, peak top molecular weight (Mp): 10390; <whole peak> number average molecular weight (Mn): 10128, weight average molecular weight (Mw): 10452, polydispersity (Mw/Mn): 1.032, peak top molecular weight (Mp): 10390.

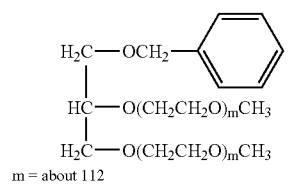

(p2)

m = about 112

Example 1-5

Into a 500 ml round-bottom flask fitted with a thermometer, a nitrogen-introducing tube, a stirrer, and a condenser tube were added 15 g of the above compound (p2), and 15 g of 5% palladium-carbon (50% hydrous product). After the replacement by nitrogen, 300 ml of methanol and 150 ml of cyclohexene were added thereto and the whole was heated to gentle reflux at 52 to 55° C. to allow to react for 5 hours. After cooling of the reaction mixture to room temperature, the palladium-carbon was removed by filtration and the filtrate was concentrated. The concentrate was crystallized by adding 50 ml of ethyl acetate and 50 ml of hexane. The resulting crystals were collected by filtration and dried to obtain the following compound (p3).

$^1$H-NMR (CDCl$_3$, internal standard: TMS) δ(ppm): 3.38 (6H, s, —CH$_3$), 3.40-3.80 (901H, m, —CH$_2$O(CH$_2$CH$_2$O)$_m$CH$_3$, CHO(CH$_2$CH$_2$O)$_m$CH$_3$, CH$_2$OH). GPC analysis: <main peak> number average molecular weight (Mn): 10069, weight average molecular weight (Mw): 10227, polydispersity (Mw/Mn): 1.016, peak top molecular weight (Mp): 10351; <whole peak> number average molecular weight (Mn): 9860, weight average molecular weight (Mw): 10294, polydispersity (Mw/Mn): 1.044, peak top molecular weight (Mp): 10351.

(p3)

H$_2$C—OH
|
HC—O(CH$_2$CH$_2$O)$_m$CH$_3$
|
H$_2$C—O(CH$_2$CH$_2$O)$_m$CH$_3$ m = about 112

Example 2

Synthesis of Mesylate Compound (Group I(b), Y=CH$_3$) (Case of R=Methyl Group, A$^1$O, A$^2$O=Oxyethylene Group, n=0, and Molecular Weight=About 10000)

Into a 200 ml round-bottom flask fitted with a thermometer, a nitrogen-introducing tube, a stirrer, a Dean-stark tube, and a condenser tube were charged 20 g (2 mmol) of the above compound (p3) and 75 g of toluene, and the whole was heated under reflux to effect azeotropic removal of water. After cooling to room temperature, 1.012 g (10 mmol) of triethylamine and 0.687 g (6 mmol) of methanesulfonyl chloride were added thereto, followed by 6 hours of reaction at 40° C. and another 1 hour of reaction at 50° C. The reaction liquid was filtered and 1.0 g of an adsorbent "KYOWAAD 1000" (manufactured by Kyowa Chemical Industry Co., Ltd.) was added to the filtrate and the whole was further stirred at 60° C. for 1 hour to adsorb triethylamine salt of methanesulfonic acid as a by-product. After filtration of the reaction liquid, the filtrate was charged into a 500 ml beaker and crystallization was carried out by adding 100 ml of ethyl acetate and 150 ml of hexane. The precipitated crystals were collected into a 300 ml beaker by filtration and dissolved under heating at 40° C. with adding 100 ml of ethyl acetate. Thereafter, 100 ml of hexane was added and crystallization was again carried out. The precipitated crystals were collected by filtration and dried to obtain the following mesylate compound (p4).

$^1$H-NMR (CDCl$_3$, internal standard: TMS) δ(ppm): 3.08 (3H, s, —SO$_3$CH$_3$), 3.38 (6H, s, —CH$_3$), 3.40-3.80 (899H, m, —CH$_2$O(CH$_2$CH$_2$O)$_m$CH$_3$, CHO(CH$_2$CH$_2$O)$_m$CH$_3$), 4.27-4.44 (2H, m, —CH$_2$OSO$_3$CH$_3$). GPC analysis: <main peak> number average molecular weight (Mn): 10054, weight average molecular weight (Mw): 10214, polydispersity (Mw/Mn): 1.016, peak top molecular weight (Mp): 10442; <whole peak> number average molecular weight (Mn): 9778, weight average molecular weight (Mw): 10252, polydispersity (Mw/Mn): 1.049, peak top molecular weight (Mp): 10442.

(p4)

$$\begin{array}{c} \text{O} \\ \| \\ \text{H}_2\text{C}—\text{OS}—\text{CH}_3 \\ \| \\ \text{O} \end{array}$$
|
HC—O(CH$_2$CH$_2$O)$_m$CH$_3$
|
H$_2$C—O(CH$_2$CH$_2$O)$_m$CH$_3$ m = about 112

Example 3

Synthesis of Amino Compound (Group II(j)) (Case of R=Methyl Group, A$^1$O, A$^2$O=Oxyethylene Group, n=0, and Molecular Weight=About 10000)

Into a 100 ml round-bottom flask fitted with a thermometer, a stirrer, and a condenser tube were charged 1 g (0.1 mmol) of the above mesylate compound (p4) and 50 ml of 28% aqueous ammonia, and the whole was stirred at 50° C. for 36 hours. The liquid temperature was raised to 65° C. and ammonia was removed with introduction of nitrogen thereinto for 2 hours. After cooling to room temperature, 10 g of sodium chloride was added thereto, followed by extraction with 10 ml of chloroform three times. The resulting chloroform layer was dried over sodium sulfate and after filtration, chloroform was removed by evaporation. Then, 100 ml of hexane was added to the resulting concentrate to effect reprecipitation. The precipitated crystals were collected by filtration and dried to obtain the following compound (p5).

$^1$H-NMR (D$_2$O, internal standard: H$_2$O=4.7 ppm) δ(ppm): 3.38 (6H, s, —C$\underline{H_3}$), 2.93-3.11 (2H, m, —C$\underline{H_2}$NH$_2$), 3.40-3.80 (899H, m, —C$\underline{H_2}$O(C$\underline{H_2}$C$\underline{H_2}$O)$_{\overline{m}}$C$\underline{H_3}$, C$\underline{H}$O(C$\underline{H_2}$CH$_2$O)$_m$CH$_3$).

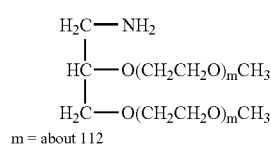

(P5)

m = about 112

Example 4

Synthesis of Aldehyde Compound (Group I(f)) (Case of R=Methyl Group, A$^1$O, A$^2$O=Oxyethylene Group, n=0, and Molecular Weight=About 10000)

Example 4-1

Into a 200 ml round-bottom flask fitted with a thermometer, a nitrogen-introducing tube, a stirrer, a Dean-stark tube, and a condenser tube were added 10 g (1 mmol) of the above mesylate compound (p4) and 40 ml of toluene, and the whole was heated under reflux to effect azeotropic removal of water, followed by cooling to room temperature. On the other hand, into a 100 ml round-bottom flask fitted with a thermometer, a nitrogen-introducing tube, a stirrer, a Dean-stark tube, and a condenser tube were added 14.8 g (0.1 mol) of 3,3-diethoxy-1-propanol and 40 ml of toluene, and the whole was heated under reflux to effect azeotropic removal of water. After cooling to room temperature, 0.36 g (15.6 mmol) of sodium was added and the whole was stirred at room temperature for 2 hours until it was dissolved. After dissolution of sodium was confirmed, the reaction liquid was poured into the round-bottom flask containing the compound (p4) from which water had been removed as above, followed by 12 hours of reaction at 110° C. After cooling of the reaction liquid to 40° C., 0.36 g (20 mmol) of ion-exchange water was added and the whole was stirred for 30 minutes. Then, 50 ml of 20% aqueous sodium chloride solution was added thereto and the aqueous layer was adjusted to pH 7.0 with 85% phosphoric acid. After the upper toluene layer was separated, the aqueous layer was extracted twice with chloroform. The toluene layer and the chloroform layer were combined and dried over sodium sulfate. After filtration, toluene and chloroform were removed by evaporation to effect concentration. The concentrate was dissolved under heating with adding 50 ml of ethyl acetate and then 50 ml of hexane was added to precipitate crystals. The resulting crystals were collected by filtration and dissolved under heating by adding 50 ml of ethyl acetate and then 50 ml of hexane was added to precipitate crystals again. This reprecipitation operation was repeated three times. Thereafter, the precipitated crystals were collected by filtration and dried to obtain the following acetal compound (p6).

$^1$H-NMR (CDCl$_3$, internal standard: TMS) δ(ppm): 1.20 (6H, t, —CH$_2$CH$_2$CH (OC$\underline{H_2}$CH$_3$)$_2$), 1.88-1.92 (2H, m, —CH$_2$C$\underline{H_2}$CH(OCH$_2$CH$_3$)$_2$), 3.38 (6H, s, —C$\underline{H_3}$), 3.40-3.80 (907H, m, —C$\underline{H_2}$O(C$\underline{H_2}$C$\underline{H_2}$O)$_m$C$\underline{H_3}$, C$\underline{H}$O(C$\underline{H_2}$C$\underline{H_2}$O)$_m$CH$_3$, —C$\underline{H_2}$—O—C$\underline{H_2}$CH$_2$CH(OCH$_2$CH$_3$)$_2$), 4.64 (1H, t, —CH$_2$CH$_2$C$\underline{H}$(OC$\underline{H_2}$CH$_3$)$_2$). GPC analysis: <main peak> number average molecular weight (Mn): 9898, weight average molecular weight (Mw): 10076, polydispersity (Mw/Mn): 1.018, peak top molecular weight (Mp): 10215; <whole peak> number average molecular weight (Mn): 9297, weight average molecular weight (Mw): 9932, polydispersity (Mw/Mn): 1.068, peak top molecular weight (Mp): 10215.

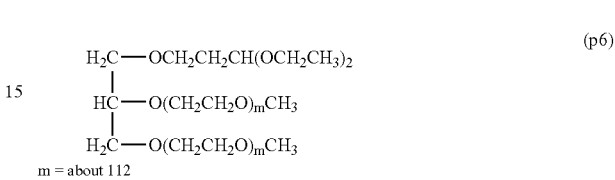

(p6)

m = about 112

Example 4-2

Into a 200 ml beaker was weighed 4 g of the resulting acetal compound (p6). Then, 80 g of ion-exchange water was added to dissolve the crystals and the solution was adjusted to pH 1.5 with 85% phosphoric acid, followed by 2 hours of stirring at room temperature. Thereafter, 16 g of sodium chloride was added and dissolved and the whole was adjusted to pH 7.0 with 30% aqueous sodium hydroxide solution, followed by extraction with chloroform. The resulting chloroform layer was dried over sodium sulfate and after filtration, chloroform was removed by evaporation to effect concentration. The concentrate was dissolved under heating by adding 30 ml of toluene and 30 ml of ethyl acetate and then 60 ml of hexane was added to precipitate crystals, which was collected by filtration. The resulting crystals were weighed into a 200 ml beaker and dissolved under heating by adding 30 ml of toluene and 30 ml of ethyl acetate and then 60 ml of hexane was added to precipitate crystals again, which was collected by filtration and dried to obtain the following aldehyde compound (p7).

$^1$H-NMR (CDCl$_3$, internal standard: TMS) δ(ppm): 2.65 (2H, m, C$\underline{H_2}$COH), 3.38 (6H, s, —C$\underline{H_3}$), 3.40-3.80 (903H, m, —C$\underline{H_2}$O(C$\underline{H_2}$C$\underline{H_2}$O)$_m$, C$\underline{H}$O(C$\underline{H_2}$C$\underline{H_2}$O)$_m$, C$\underline{H_2}$O CH$_2$CH$_2$COH), 9.78 (1H, m, CH$_2$CO$\underline{H}$).

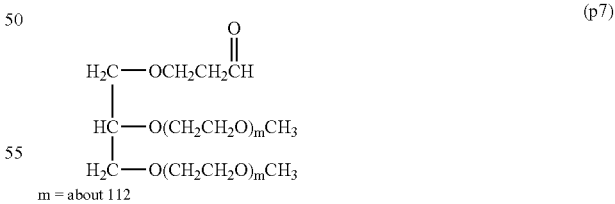

(p7)

m = about 112

Example 5

Into 50 ml of 100 mm sodium dihydrogen phosphate was added and dissolved 63 mg (20 mM) of sodium cyanotrihydroborate. To 1 ml of the solution were added 5.0 mg (0.1 μmol) of OVA (ALUBUMIN, CHIKEN EGG, molecular weight about 40000) and 100 mg of the aldehyde compound (p7), followed by 12 hours of stirring at room temperature. The reaction liquid was diluted five times with ion-exchange water and 20 μl of the diluted solution was mixed with 20 μl of a Tris-SDS sample-treating liquid, followed by 2.5 minutes of heating on a boiling water bath. The treated liquid was analyzed by a sodium dodecyl sulfate-polyacrylamide gel electrophoresis (4 to 20%). The gel was stained by CBB staining. The results were shown in FIG. 1. (A) is a lane of OVA+aldehyde compound, (B) a lane of OVA alone, and (C) a lane of a marker (Bio-rad Broad range SDS-PAGE standards) which shows bands of molecular weights of 201000, 130000, 94000, 48600, 36400, 29800, 20600, and 600 from the top.

From these results, a band of the starting OVA did not remain but bands of molecular weights corresponding to the cases that OVA was modified with the compound (p6) at 1 to 15 places per one molecule were observed in (A).

Example 6

For evaluating stability of the compounds of the invention, the following model compound was synthesized and the stability was compared.

Example 6-1

In 50 ml of methanol was dissolved 63 mg (20 mM) of sodium cyanotrihydroborate. Into 2 ml of the solution were added 0.5 g of the aldehyde compound (p7) and 50 μl of n-butylamine, followed by 18 hours of stirring at room temperature. Methanol was removed by evaporation to effect concentration and then the concentrate was extracted by adding 20 ml of chloroform and 20 ml of 20% aqueous sodium chloride. The extraction operation was repeated three times. The resulting chloroform layer was dried over sodium sulfate and after filtration, concentrated. The resulting concentrate was dissolved by adding 20 ml of ethyl acetate and then 30 ml of hexane was added to precipitate crystals, which was collected by filtration. The resulting crystals were weighed into a 100 ml beaker and dissolved under heating with adding 20 ml of ethyl acetate and then 20 ml of hexane was added to precipitate crystals again, which was collected by filtration and dried to obtain the following compound (p8).

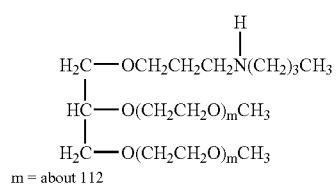

(p8)

m = about 112

Example 6-2

Evaluation of Stability (Accelerated Aging Test)

Figure 2:
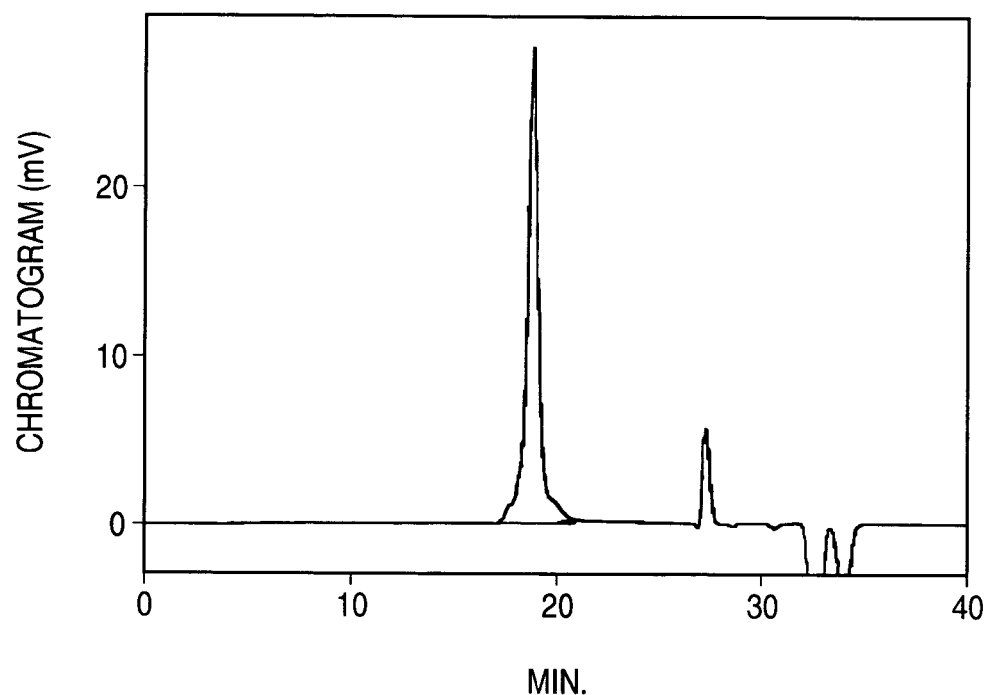
FIG. 2 is a chart illustrating a result of GPC measurement before an accelerated aging test of the compound p-8.
Figure 3:
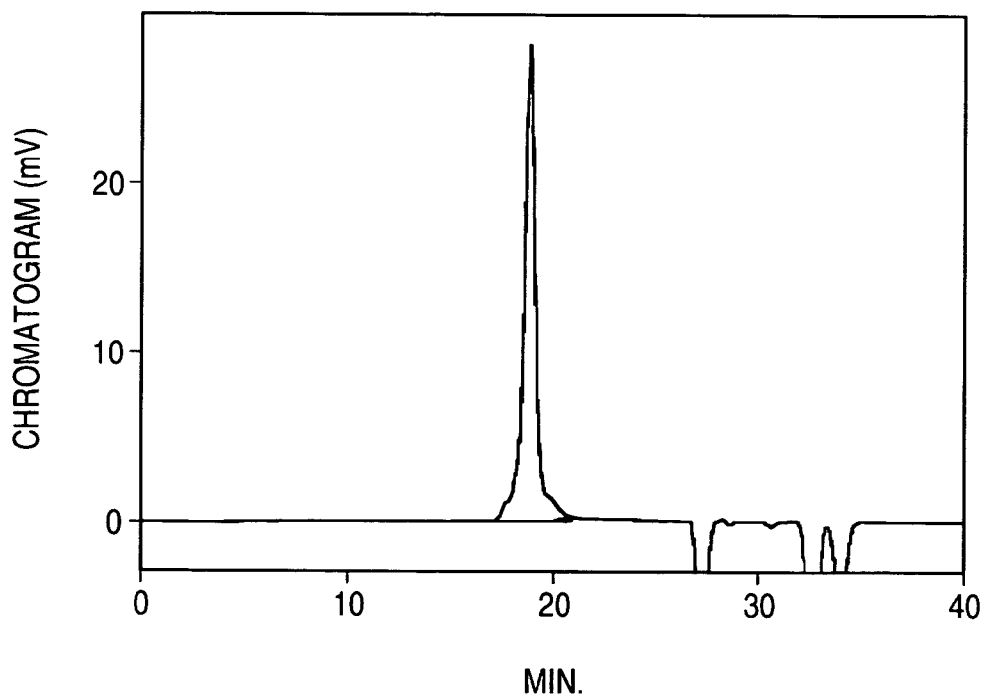
FIG. 3 is a chart illustrating a result of GPC measurement after an accelerated aging test of the compound p-8.

The synthesized above compound (p8) was weighed in an amount of 12 mg, and 1 ml of 100 mM phosphate buffer (pH=8.8) was added thereto, followed by 12 hours of stirring on a water bath at 75° C. GPC measurement was carried out before starting and after completion of stirring. The results are shown in FIG. 2 and FIG. 3. FIG. 2 is a GPC chart of the sample before starting and FIG. 3 is a GPC chart of the sample of (p8) after heating.

Comparative Example 1

The following compound (p9) having a molecular weight of about 10700 purchased from Shearwater Polymers, Inc. was weighed in an amount of 107 mg, and 10 μl of n-butylamine and 1 ml of chloroform were added thereto, followed by 18 hours of stirring at room temperature. Chloroform was removed by evaporation to effect concentration and then the concentrate was dissolved under heating with adding 20 ml of ethyl acetate and then 30 ml of hexane was added to precipitate crystals, which was collected by filtration. The resulting crystals were weighed into a 100 ml beaker and dissolved under heating with adding 20 ml ethyl acetate and then 20 ml of hexane was added to precipitate crystals again, which was collected by filtration and dried to obtain the following compound (p10).

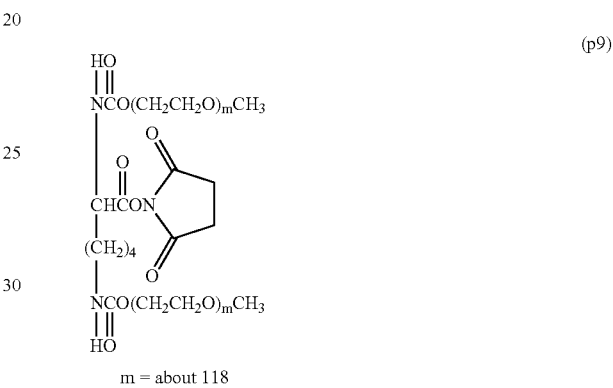

(p9)

m = about 118

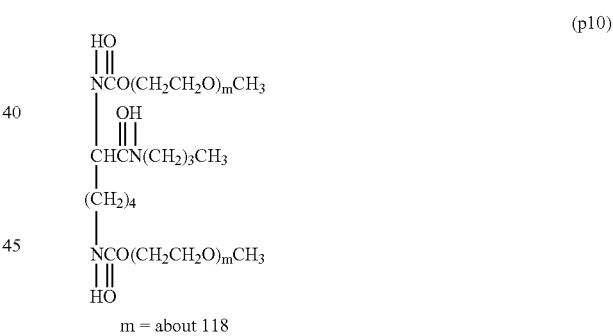

(p10)

m = about 118

Figure 4:
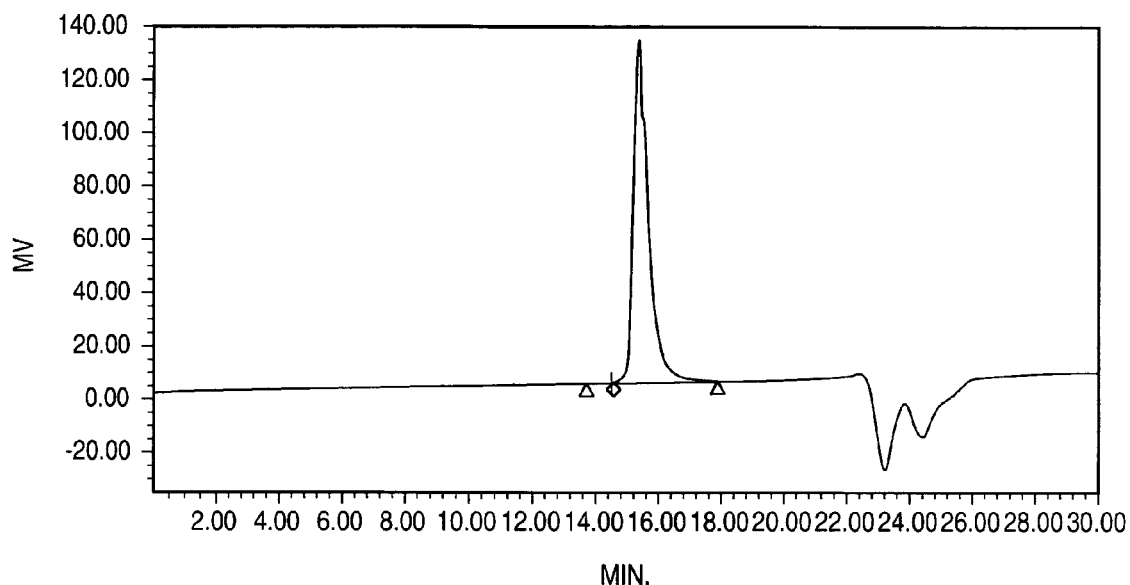
FIG. 4 is a chart illustrating a result of GPC measurement before an accelerated aging test of the compound p-10.
Figure 5:
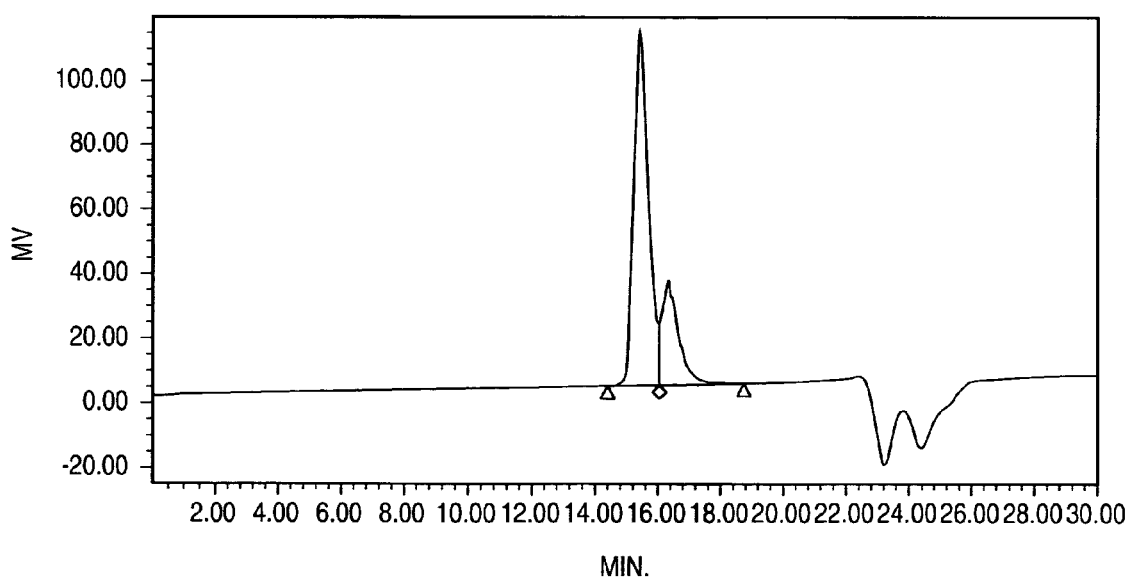
FIG. 5 is a chart illustrating a result of GPC measurement after an accelerated aging test of the compound p-10.

Using the above synthesized compound (p10), the same operations as in Example 6-2 were carried out and GPC measurement was conducted. The results are shown in FIG. 4 and FIG. 5. FIG. 4 is a GPC chart of the sample of (p10) before starting and FIG. 5 is a GPC chart of the sample of (p10) after heating.

From the results of FIG. 2 and FIG. 3, the compounds of the invention did not hydrolyzed and exhibited a high stability. On the other hand, from the results of FIG. 4 and FIG. 5, a compound having ½ molecular weight was formed in an amount of about 25% in the case of Comparative Example, (p10), which showed that the urethane bond was cleaved and the branched polyethylene glycol was decomposed into a single chain.

Example 7

Synthesis of Compound (p) (Case of R=Methyl Group, $A^1O$, $A^2O$=Oxyethylene Group, n=0, and Molecular Weight=About 19000)

Example 7-1

In a similar manner to Example 1-3, 2850 g (64.8 mol) of ethylene oxide was charged and the following compound (p11) was obtained.

$^1$H-NMR (CDCl$_3$, internal standard: TMS) δ(ppm): 3.40-3.80 (1733H, m, —C$\underline{H_2}$O(C$\underline{H_2}$C$\underline{H_2}$O)$_m$H, C$\underline{H}$O(C$\underline{H_2}$C$\underline{H_2}$O)$_m$H, C$\underline{H_2}$OCH$_2$Ph), 4.54 (2H, s, —C$\underline{H_2}$Ph), 7.27-7.38 (5H, m, —CH$_2$P$\underline{h}$). GPC analysis: <main peak> number average molecular weight (Mn): 18521, weight average molecular weight (Mw): 18758, polydispersity (Mw/Mn): 1.013, peak top molecular weight (Mp): 19108; <whole peak> number average molecular weight (Mn): 18403, weight average molecular weight (Mw): 18913, polydispersity (Mw/Mn): 1.028, peak top molecular weight (Mp): 19108.

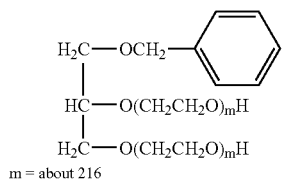

(p11)

m = about 216

Example 7-2

In a similar manner to Example 1-4, the following compound (p12) was obtained using 100 g (5 mmol) of (p11), 320 g of toluene, 5.06 g (50 mmol) of triethylamine, 3.44 g (30 mmol) of methanesulfonyl chloride, and 9.65 g (50 mmol) of 28% methanol solution of sodium methoxide.

$^1$H-NMR (CDCl$_3$, internal standard: TMS) δ(ppm): 3.38 (6H, s, —C$\underline{H_3}$), 3.40-3.80 (1733H, m, —C$\underline{H_2}$O(CH$_2$CH$_2$O)$_m$C$\underline{H_3}$, C$\underline{H}$O(CH$_2$CH$_2$O)$_m$CH$_3$, C$\underline{H_2}$OC$\underline{H_2}$Ph), 4.54 (2H, s, —C$\underline{H_2}$Ph), 7.27-7.38 (5H, m, —CH$_2$P$\underline{h}$). GPC analysis: <main peak> number average molecular weight (Mn): 18365, weight average molecular weight (Mw): 18602, polydispersity (Mw/Mn): 1.013, peak top molecular weight (Mp): 18992; <whole peak> number average molecular weight (Mn): 18290, weight average molecular weight (Mw): 18861, polydispersity (Mw/Mn): 1.031, peak top molecular weight (Mp): 18992.

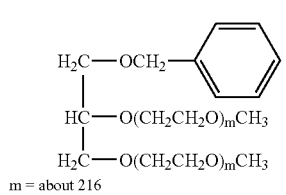

(p12)

m = about 216

Example 7-3

The following compound (p13) was obtained in a similar manner to Example 1-5.

$^1$H-NMR (CDCl$_3$, internal standard: TMS) δ(ppm): 3.38 (6H, s, —C$\underline{H_3}$), 3.40-3.80 (1733H, m, —C$\underline{H_2}$O(CH$_2$CH$_2$O)$_m$C$\underline{H_3}$, C$\underline{H}$O(CH$_2$CH$_2$O)$_m$CH$_3$, C$\underline{H_2}$OH). GPC analysis: <main peak> number average molecular weight (Mn): 18395, weight average molecular weight (Mw): 18632, polydispersity (Mw/Mn): 1.013, peak top molecular weight (Mp): 18989; <whole peak> number average molecular weight (Mn): 18146, weight average molecular weight (Mw): 18750, polydispersity (Mw/Mn): 1.033, peak top molecular weight (Mp): 18989.

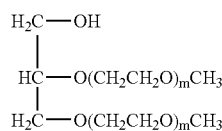

(p13)

m = about 216

Example 8

Synthesis of Carboxyl Compound (Group II(k)) and Succinimide Ester Compound (Group I(a)) (Case of R=Methyl Group, $A^1O$, $A^2O$=Oxyethylene Group, n=0, and Molecular Weight=About 19000)

Into a 200 ml round-bottom flask fitted with a thermometer, a nitrogen-introducing tube, a stirrer, a Dean-stark tube, and a condenser tube were charged 20 g (1.0 mmol) of the above compound (p13), 50 mg of sodium acetate, and 100 ml of toluene, and the whole was heated under reflux to effect azeotropic removal of water. Then, 137 mg (1.2 mmol) of glutaric anhydride was added to the reaction liquid, followed by 12 hours of reaction at 105° C. After completion of the reaction, the reaction liquid was cooled to 40° C. and 150 mg (1.3 mmol) of N-hydroxysuccinimide and 289 mg (1.4 mmol) of dicyclohexylcarbodiimide were added thereto, followed by 6 hours of reaction. The reaction liquid was filtered to remove precipitated urea and, after addition of 50 ml of ethyl acetate to the filtrate, 150 ml of hexane was added to precipitate crystals. The precipitated crystals were collected by filtration and dissolved under heating with adding 100 ml of ethyl acetate. Then, 100 ml of hexane was added thereto to crystallize the product again. The precipitated crystals were collected by filtration and dried to obtain the following succinimide ester compound (p14).

$^1$H-NMR (CDCl$_3$, internal standard: TMS) δ(ppm): 2.07 (2H, m, —OCOCH$_2$C$\underline{H_2}$CH$_2$COON—), 2.50 (2H, t, —OCOC$\underline{H_2}$CH$_2$CH$_2$COON—), 2.72 (2H, t, —OCOCH$_2$CH$_2$C$\underline{H_2}$COON—), 2.84 (4H, s, succinimide), 3.38 (6H, s, —C$\underline{H_3}$), 3.40-3.80 (1731H, m, —C$\underline{H_2}$O(CH$_2$CH$_2$O)$_m$CH$_3$, C$\underline{H}$O(CH$_2$CH$_2$O)$_m$CH$_3$), 4.10-4.30 (2H, m, —C$\underline{H_2}$OCOCH$_2$CH$_2$CH$_2$COON—).

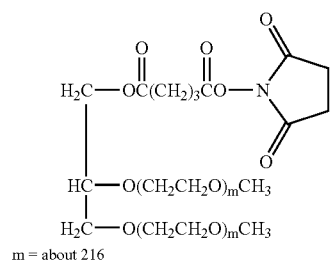

(p14)

m = about 216

Example 9

Synthesis of p-nitrophenyl Carbonate Compound (Group I(d)) (Case of R=Methyl Group, $A^1O$, $A^2O$=Oxyethylene Group, n=0, and Molecular Weight=About 19000)

Into a 200 ml round-bottom flask fitted with a thermometer, a nitrogen-introducing tube, a stirrer, a Dean-stark tube, and a condenser tube were charged 20 g (1.0 mmol) of the above compound (p13) and 100 ml of toluene, and the whole was heated under reflux to effect azeotropic removal of water. The reaction liquid was cooled to 80° C. and triethylamine and p-nitrophenyl chloroformate were added to thereto, followed by 5 hours of reaction at 80° C. After completion of the reaction, the reaction liquid was filtered and, after addition of 100 ml of ethyl acetate to the filtrate, 200 ml of hexane was added to precipitate crystals. The precipitated crystals were collected by filtration and dissolved under heating with adding 100 ml of ethyl acetate. Then, 100 ml of hexane was added thereto to crystallize the product again. The crystallization operation was repeated five times in total. The crystals collected by filtration were dried to obtain the following p-nitrophenyl carbonate compound (p15).

$^1$H-NMR (CDCl$_3$, internal standard: TMS) δ(ppm): 3.38 (6H, s, —CH$_3$), 3.40-3.80 (1731H, m, —CH$_2$O(CH$_2$CH$_2$O)$_m$CH$_3$, CHO(CH$_2$CH$_2$O)$_m$CH$_3$), 4.30-4.50 (2H, m, —CH$_2$OCOOPhNO$_2$), 7.39 (2H, d, -PhNO$_2$), 8.28 (2H, d, -PhNO$_2$).

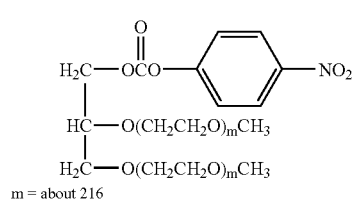

(p15)

m = about 216

Example 10

Synthesis of Compound (p) (Case of R=Methyl Group, $A^1O$, $A^2O$=Oxyethylene Group, n=about 15, and Molecular Weight=About 19500)

Into a 500 ml round-bottom flask fitted with a thermometer, a nitrogen-introducing tube, a stirrer, a Dean-stark tube, and a condenser tube were charged 67 g (3.5 mmol) of the compound (p13) obtained in Example 7-3 and 400 ml of toluene, and the whole was heated under reflux to effect azeotropic removal of water. The reaction liquid was cooled to 40° C. and 0.41 g (2.1 mmol) of a 28% methanol solution of sodium methoxide was added thereto. After heating to 70° C., about 200 ml of a mixed solution of toluene-methanol was removed by evaporation with nitrogen bubbling. The solution was charged into a 5 L autoclave and the atmosphere was replaced by nitrogen, followed by heating to 100° C. Then, 9.2 g (0.2 mol) of ethylene oxide was added thereto at 100 to 150° C. under a pressure of 1 MPa or lower, followed by continuation of the reaction for another 3 hours. Unreacted ethylene oxide gas and toluene were removed under reduced pressure, then the whole was cooled to 60° C. and adjusted to pH 7.5 with a 85% aqueous phosphoric acid solution to obtain the following compound (p16).

$^1$H-NMR (CDCl$_3$, internal standard: TMS) δ(ppm): 3.38 (6H, s, —CH$_3$), 3.40-3.80 (1853H, m, —CH$_2$O(CH$_2$CH$_2$O)$_m$CH$_3$, CHO(CH$_2$CH$_2$O)$_m$CH$_3$, —CH$_2$O(CH$_2$CH$_2$O)$_n$H). GPC analysis: <main peak> number average molecular weight (Mn): 19153, weight average molecular weight (Mw): 19462, polydispersity (Mw/Mn): 1.016, peak top molecular weight (Mp): 19612; <whole peak> number average molecular weight (Mn): 18473, weight average molecular weight (Mw): 19087, polydispersity (Mw/Mn): 1.033, peak top molecular weight (Mp): 19612.

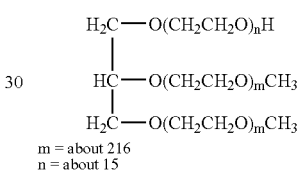

(p16)

m = about 216
n = about 15

Example 11

Synthesis of Mesylate Compound (Group I(b), Y=CH$_3$) (Case of R=Methyl Group, $A^1O$, $A^2O$=Oxyethylene Group, n=About 15, and Molecular Weight=About 19500)

Into a 200 ml round-bottom flask fitted with a thermometer, a nitrogen-introducing tube, a stirrer, a Dean-stark tube, and a condenser tube were charged 10 g (0.5 mmol) of the above compound (p16) and 75 g of toluene, and the whole was heated under reflux to effect azeotropic removal of water. After cooling to room temperature, 0.253 g (2.5 mmol) of triethylamine and 0.172 g (1.5 mmol) of methanesulfonyl chloride were added thereto, followed by 6 hours of reaction at 40° C. and another 1 hour of reaction at 50° C. The reaction liquid was filtered and 0.5 g of an adsorbent "KYOWAAD 1000" was added to the filtrate and the whole was stirred at 60° C. for 1 hour to adsorb triethylamine salt of methanesulfonic acid as a by-product. After filtration of the reaction liquid, the filtrate was charged into a 300 ml beaker and crystallization was carried out with adding 50 ml of ethyl acetate and 70 ml of hexane. The precipitated crystals were collected into a 300 ml beaker by filtration and dissolved under heating at 40° C. with adding 50 ml of ethyl acetate. Thereafter, 50 ml of hexane was added and crystallization was again carried out. The precipitated crystals were collected by filtration and dried to obtain the following mesylate compound (p17).

$^1$H-NMR (CDCl$_3$, internal standard: TMS) δ(ppm): 3.08 (3H, s, —SO$_3$CH$_3$), 3.38 (6H, s, —CH$_3$), 3.40-3.80 (1851H, m, —CH$_2$O(CH$_2$CH$_2$O)$_m$CH$_3$, CHO(CH$_2$CH$_2$O)$_m$CH$_3$, —CH$_2$O(CH$_2$CH$_2$O)$_n$SOOCH$_3$), 4.37-4.39 (2H, m, —CH$_2$O ($CH_2CH_2O)_{n-1}CH_2\underline{CH_2}OSOOCH_3$). GPC analysis: <main peak> number average molecular weight (Mn): 19253, weight average molecular weight (Mw): 19601, polydispersity (Mw/Mn): 1.018, peak top molecular weight (Mp): 19770; <whole peak> number average molecular weight (Mn): 18400, weight average molecular weight (Mw): 19140, polydispersity (Mw/Mn): 1.040, peak top molecular weight (Mp): 19770.

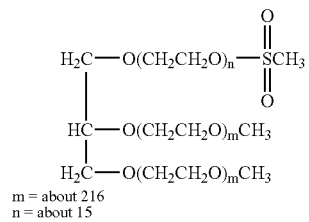

(p17)

m = about 216
n = about 15

Example 12

Synthesis of Aldehyde Compound (Group I(f)) (Case of R=Methyl Group, $A^1O$, $A^2O$=Oxyethylene Group, n=About 15, and Molecular Weight=About 19500)

Example 12-1

Into a 200 ml round-bottom flask fitted with a thermometer, a nitrogen-introducing tube, a stirrer, a Dean-stark tube, and a condenser tube were added 10 g (0.5 mmol) of the above mesylate compound (p17) and 40 ml of toluene, and the whole was heated under reflux to effect azeotropic removal of water, followed by cooling to room temperature. On the other hand, into a 100 ml round-bottom flask fitted with a thermometer, a nitrogen-introducing tube, a stirrer, a Dean-stark tube, and a condenser tube were added 7.4 g (50 mmol) of 3,3-diethoxy-1-propanol and 40 ml of toluene, and the whole was heated under reflux to effect azeotropic removal of water. After cooling to room temperature, 0.17 g (7.4 mmol) of sodium was added and the whole was stirred at room temperature for 2 hours until it was dissolved. After dissolution of sodium was confirmed, the reaction liquid was poured into the round-bottom flask containing the compound (p17) from which water had been removed as above, followed by 4 hours of reaction at 70° C. After cooling of the reaction liquid to 40° C., 0.18 g (10 mmol) of ion-exchange water was added and the whole was stirred for 30 minutes. Then, 30 ml of 20% aqueous sodium chloride solution was added thereto and the aqueous layer was adjusted to pH 7.0 with 85% phosphoric acid. After the upper toluene layer was separated, the aqueous layer was extracted twice with chloroform. The toluene layer and the chloroform layer were combined and dried over sodium sulfate. After filtration, toluene and chloroform were removed by evaporation to effect concentration. The concentrate was dissolved under heating with adding 50 ml of ethyl acetate and then 50 ml of hexane was added to precipitate crystals. The resulting crystals were collected by filtration and then dissolved under heating with adding 50 ml of ethyl acetate and then 50 ml of hexane was added to precipitate crystals again. This reprecipitation operation was repeated three times. Thereafter, the precipitated crystals were collected by filtration and dried to obtain the following acetal compound (p18).

$^1$H-NMR (CDCl$_3$, internal standard: TMS) δ(ppm): 1.20 (6H, t, —CH$_2$CH$_2$CH(OCH$_2$$\underline{CH_3}$)$_2$), 1.88-1.92 (2H, m, —CH$_2$$\underline{CH_2}$CH(OCH$_2$CH$_3$)$_2$), 3.38 (6H, s, —$\underline{CH_3}$) 3.40-3.80 (1857H, m, —$\underline{CH_2O(CH_2CH_2O)_mCH_3}$, $\underline{CHO}$(CH$_2$CH$_2$O)$_m$CH$_3$, —$\underline{CH_2}$O($\underline{CH_2CH_2O})_n\underline{CH_2}$CH$_2$CH(O$\underline{CH_2CH_3}$)$_2$), 4.64 (1H, t, —CH$_2$CH$_2$$\underline{CH}$(OCH$_2$CH$_3$)$_2$). GPC analysis: <main peak> number average molecular weight (Mn): 19318, weight average molecular weight (Mw): 19699, polydispersity (Mw/Mn): 1.020, peak top molecular weight (Mp): 19770; <whole peak> number average molecular weight (Mn): 18302, weight average molecular weight (Mw): 19168, polydispersity (Mw/Mn): 1.047, peak top molecular weight (Mp): 19770.

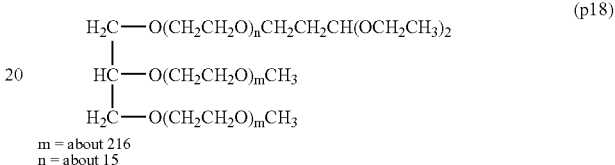

(p18)

m = about 216
n = about 15

Example 12-2

Into a 100 ml beaker was weighed 2 g of the resulting acetal compound (p18). Then, 40 g of ion-exchange water was added to dissolve the crystals and the solution was adjusted to pH 1.5 with 85% phosphoric acid, followed by 2 hours of stirring at room temperature. Thereafter, 8 g of sodium chloride was added and dissolved and the whole was adjusted to pH 7.0 with 30% aqueous sodium hydroxide solution, followed by extraction with chloroform three times. The resulting chloroform layer was dried over sodium sulfate and after filtration, chloroform was removed by evaporation to effect concentration. The concentrate was dissolved under heating with adding 30 ml of toluene and 30 ml of ethyl acetate and then 60 ml of hexane was added to precipitate crystals, which was collected by filtration. The resulting crystals were weighed into a 200 ml beaker and dissolved under heating with adding 30 ml of toluene and 30 ml of ethyl acetate and then 60 ml of hexane was added to precipitate crystals again, which was collected by filtration and dried to obtain the following aldehyde compound (p19).

$^1$H-NMR (CDCl$_3$, internal standard: TMS) δ(ppm): 2.66-2.69 (2H, m, $\underline{CH_2}$COH), 3.38 (6H, s, —$\underline{CH_3}$), 3.40-3.80 (1855H, m, —$\underline{CH_2O(CH_2CH_2O)_mCH_3}$, $\underline{CHO}$(CH$_2$CH$_2$O)$_m$CH$_3$, —$\underline{CH_2}$O($\underline{CH_2CH_2O})_n\underline{CH_2}$CH$_2$COH), 9.79 (1H, t, —CH$_2$CH$_2$$\underline{C}$OH).

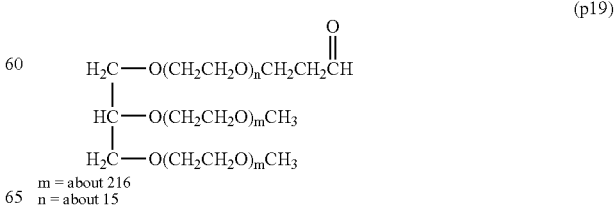

(p19)

m = about 216
n = about 15

Example 13

Synthesis of Mesylate Compound (Group I(b), Y=CH$_3$) (Case of R=Methyl Group, A$^1$O, A$^2$O=Oxyethylene Group, n=0, and Molecular Weight=About 19000)

Using the compound (p13) as a starting material, the following mesylate compound (p20) was obtained in a similar manner to Example 2.

$^1$H-NMR (CDCl$_3$, internal standard: TMS) δ(ppm): 3.08 (3H, s, —SO$_3$CH$_3$), 3.38 (6H, s, —CH$_3$), 3.40-3.80 (1731H, m, —CH$_2$O(CH$_2$CH$_2$O)$_m$CH$_3$, CHO(CH$_2$CH$_2$O)$_m$CH$_3$), 4.27-4.44 (2H, m, —CH$_2$OSO$_3$CH$_3$). GPC analysis: <main peak> number average molecular weight (Mn): 18435, weight average molecular weight (Mw): 18682, polydispersity (Mw/Mn): 1.013, peak top molecular weight (Mp): 18740; <whole peak> number average molecular weight (Mn): 18081, weight average molecular weight (Mw): 18721, polydispersity (Mw/Mn): 1.035, peak top molecular weight (Mp): 18740.

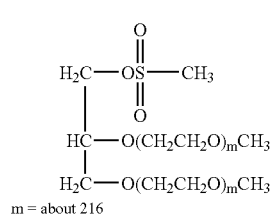

(p20)

m = about 216

Example 14

Synthesis of Amino Compound (Group II(j)) (Case of R=Methyl Group, A$^1$O, A$^2$O=Oxyethylene Group, n=0, and Molecular Weight=About 19000)

Using the compound (p20) as a starting material, the following amino compound (p21) was obtained in a similar manner to Example 3.

$^1$H-NMR (D$_2$O, internal standard: H$_2$O=4.7 ppm) δ(ppm): 3.38 (6H, s, —CH$_3$), 2.93-3.11 (2H, m, —CH$_2$NH$_2$), 3.40-3.80 (1731H, m, —CH$_2$O(CH$_2$CH$_2$O)$_m$CH$_3$, CHO(CH$_2$CH$_2$O)$_m$CH$_3$).

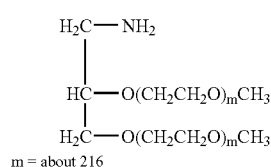

(P21)

m = about 216

Example 15

Synthesis Of Maleimide Compound (Group I(e)) (Case of R=Methyl Group, A$^1$O, A$^2$O=Oxyethylene Group, n=0, and Molecular Weight=About 19000)

Into a 100 ml round-bottom flask fitted with a thermometer, a nitrogen-introducing tube, a stirrer, and a condenser tube were charged 7.5 g (0.35 mmol) of the above compound (p21), 35 ml of ethyl acetate, and 73 μl of triethylamine, and the whole was heated at 45° C. to dissolve them. Then, 0.14 g (0.525 mmol) of N-succinimidyl 3-maleimidopropionate was added thereto, followed by 4 hours of reaction at 45° C. After completion of the reaction, 0.5 g of an adsorbent "KYOWAAD 700" and 0.5 g of "KYOWAAD 1000" were added thereto and the whole was stirred at 45° C. for another 1 hour. The reaction liquid was filtrated and 50 ml of hexane was added to the filtrate to precipitate crystals, which was collected by filtration. The resulting crystals were weighed into a 200 ml beaker and dissolved under heating with adding 50 ml of ethyl acetate. Then, 50 ml of hexane was added to precipitate crystals again, which were collected by filtration and dried to obtain the following maleimide compound (p22).

$^1$H-NMR (CDCl$_3$, internal standard: TMS) δ(ppm): 2.51 (2H, t, —NHCOCH$_2$CH$_2$), 3.38 (6H, s, —CH$_3$), 3.40-3.80 (1735H, m, —CH$_2$O(CH$_2$CH$_2$O)$_m$CH$_3$, CHO(CH$_2$CH$_2$O)$_m$CH$_3$, CH$_2$NHCOCH$_2$CH$_2$), 6.69 (2H, s, CH=CH), 6.86 (1H, t, CH$_2$NHCOCH$_2$CH$_2$. GPC analysis: <main peak> number average molecular weight (Mn): 18425, weight average molecular weight (Mw): 18672, polydispersity (Mw/Mn): 1.013, peak top molecular weight (Mp): 18742; <whole peak> number average molecular weight (Mn): 17924, weight average molecular weight (Mw): 19086, polydispersity (Mw/Mn): 1.065, peak top molecular weight (Mp): 18742.

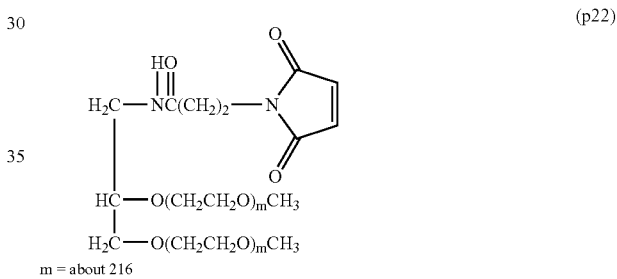

(p22)

m = about 216

Example 16

Synthesis of Compound (p) (Case of R=Methyl Group, A$^1$O, A$^2$O=Oxyethylene Group, n=0, and Molecular Weight=About 20000, About 45000)

Example 16-1

To a 1000 ml round-bottom flask fitted with a thermometer, a nitrogen-introducing tube, and a stirrer were added 132.2 g (1.0 mol) of 2,2-dimethyl-1,3-dioxolane-4-methanol, 202.5 g (1.05 mol) of a 28% methanol solution of sodium methoxide, and 500 ml of toluene. With introduction of nitrogen thereinto, toluene was refluxed under reduced pressure for 1 hour to remove the methanol by evaporation. With maintaining the solution at 80° C., 126.6 g (1.0 mol) of benzyl chloride was added dropwise over a period of 2 hours using a dropping funnel, followed by another 2 hours of reaction. After completion of the reaction, the temperature was lowered to 60° C. and 10 g of KYOWAAD 600 was added, followed by 1 hour of stirring. After filtration of the reaction liquid, the solvent was removed and the residue was purified by distillation (b.p. 93-95° C./266 Pa) to obtain 4-(benzyloxymethyl)-2,2-dimethyl-1,3-dioxolane.

$^1$H-NMR (CDCl$_3$, internal standard: TMS) δ(ppm): 1.36, 1.42 (3H, 3H, s, C(CH$_3$)$_2$), 3.45-3.57 (2H, m, CH$_2$O—C(CH$_3$)$_2$), 3.73-3.76 (1H, m, CHO—C(CH$_3$)$_2$), 4.03-4.07, 4.28-4.32 (2H, m, CH$_2$O—CH$_2$Ph), 4.57 (2H, q, —CH$_2$Ph), 7.15-7.40 (5H, m, —CH$_2$Ph) (Ph represents a phenyl group).

Example 16-2

To 222 g (1.0 mol) of 4-(benzyloxymethyl)-2,2-dimethyl-1,3-dioxolane was added 400 g of distilled water, and the whole was adjusted to pH 2 with phosphoric acid. With introduction of nitrogen thereinto, the solution was heated to 70° C. After 2 hours of reaction, the solution was adjusted to pH 7.0 with sodium hydroxide. Thereto was charged 1 L of chloroform and extraction was carried out. Then, the chloroform layer was dried over magnesium sulfate and concentrated. Thereafter, the concentrate was filtrated to remove salts, and thereby 3-benzyloxy-1,2-propanediol was obtained. The NMR data thereof are the same as those in Example 1-2.

Example 16-3

To a 300 ml round-bottom flask fitted with a thermometer, a nitrogen-introducing tube, a stirrer, and a pressure-reducing line were added 27.3 g (0.15 mol) of 3-benzyloxy-1,2-propanediol, 200 g of dry toluene, and 0.77 g (33.4 mmol: 22.3 mol %) of sodium. With introduction of nitrogen thereinto, the temperature was raised to 35° C. to dissolve sodium. The solution was charged into a 5 L autoclave which had been thoroughly dried beforehand and the atmosphere was replaced by nitrogen, followed by heating to 100° C. Then, 3090 g of ethylene oxide was introduced under pressure thereto at 100 to 150° C. under a pressure of 1 MPa or lower, followed by continuation of the reaction for another 1.5 hours. Unreacted ethylene oxide gas and toluene were removed under reduced pressure, then the whole was cooled to 70° C. Then, 2.0 kg of the reaction liquid was taken out of the autoclave and the reaction liquid taken out was adjusted to pH 7.5 with 85% aqueous phosphoric acid solution to obtain the following compound (p23).

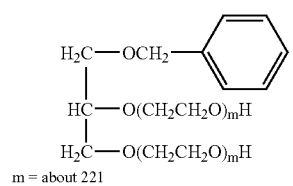

(p23)
m = about 221

$^1$H-NMR (CDCl$_3$, internal standard: TMS) δ(ppm): 3.40-3.80 (1773H, m, —CH$_2$O(CH$_2$CH$_2$O)$_m$H, CHO(CH$_2$CH$_2$O)$_m$H, CH$_2$OCH$_2$Ph), 4.54 (2H, s, —CH$_2$Ph), 7.27-7.38 (5H, m, —CH$_2$Ph). GPC analysis: <main peak> number average molecular weight (Mn): 18920, weight average molecular weight (Mw): 19154, polydispersity (Mw/Mn): 1.012, peak top molecular weight (Mp): 19639; <whole peak> number average molecular weight (Mn): 18777, weight average molecular weight (Mw): 19086, polydispersity (Mw/Mn): 1.017, peak top molecular weight (Mp): 19639.

Example 16-4

Into a 2 L round-bottom flask fitted with a thermometer, a nitrogen-introducing tube, a stirrer, a Dean-stark tube, and a condenser tube were added 200 g (10 mmol) of the above compound (p23) and 1000 g of toluene, and the whole was heated under reflux to effect azeotropic removal of 200 g of toluene and water. After cooling to room temperature, 10.12 g (100 mmol) of triethylamine was added and the whole was heated to 40° C. Then, 6.87 g (60 mmol) of methanesulfonyl chloride was added thereto, followed by 3 hours of reaction at 40° C. After completion of the reaction, 19.28 g (100 mmol) of a 28% methanol solution of sodium methoxide was added to the reaction liquid, followed by 3 hours of reaction at 40° C. The pressure was reduced with maintaining the reaction liquid at 40° C. to remove about 200 g of a mixed solution of methanol/toluene by evaporation and then salts were removed by filtration. Then, 500 g of toluene was added to the filtrate and the mixture was transferred into a 2 L round-bottom flask fitted with a thermometer, a nitrogen-introducing tube, a stirrer, a Dean-stark tube, and a condenser tube. The whole was heated under reflux to effect azeotropic removal of 200 g of toluene and water. After cooling to room temperature, 10.12 g (100 mmol) of triethylamine was added and the whole was heated to 40° C. Then, 8.89 g (60 mmol) of methanesulfonyl chloride was added thereto, followed by 3 hours of reaction at 40° C. After completion of the reaction, 19.28 g (100 mmol) of a 28% methanol solution of sodium methoxide was added to the reaction liquid, followed by 3 hours of reaction at 40° C. The pressure was reduced with maintaining the reaction liquid at 40° C. to remove about 200 g of a mixed solution of methanol/toluene by evaporation and then salts were removed by filtration. The filtrate was heated to 50° C. and then 200 g of 25% aqueous sodium chloride was added thereto. After stirring, the whole was left on standing to be separated into layers and the lower aqueous layer was removed. The operation of washing with water was repeated twice. The upper toluene layer was dried over magnesium sulfate and then filtrated, and 1 L of ethyl acetate was added to the filtrate. Then, hexane was added thereto until crystals were precipitated. The crystals were collected by filtration and dried to obtain the following compound (p24).

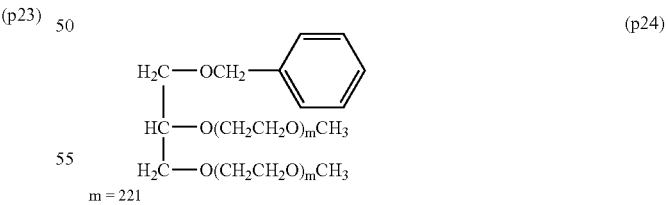

(p24)
m = 221

$^1$H-NMR (CDCl$_3$, internal standard: TMS) δ(ppm): 3.38 (6H, s, —CH$_3$), 3.40-3.80 (1773H, m, —CH$_2$O(CH$_2$CH$_2$O)$_m$CH$_3$, CHO(CH$_2$CH$_2$O)$_m$CH$_3$, CH$_2$OCH$_2$Ph), 4.54 (2H, s, —CH$_2$Ph), 7.27-7.38 (5H, m, —CH$_2$Ph). GPC analysis: <main peak> number average molecular weight (Mn): 19070, weight average molecular weight (Mw): 19306, polydispersity (Mw/Mn): 1.012, peak top molecular weight (Mp): 19786; <whole peak> number average molecular weight (Mn): 18911, weight average molecular weight (Mw): 19256, polydispersity (Mw/Mn): 1.018, peak top molecular weight (Mp): 19786.

Example 16-5

Into a pressure filter was charged 120 g of 5% palladium-carbon (50% hydrous product, manufactured by N. E. M. Cat), and solvent substitution was carried out four times with 500 ml of anhydrous methanol under replacement by nitrogen to effect removal of water from the palladium-carbon. Into a 2 L round-bottom flask fitted with a thermometer, a nitrogen-introducing tube, a stirrer, and a condenser tube were added 100 g of the above compound (p24), and the whole amount of the palladium-carbon which had been subjected to solvent substitution. After replacement by nitrogen, 1200 ml of anhydrous methanol and 500 ml of cyclohexene were added thereto and the whole was heated to 30° C. to be allowed to react for 3.5 hours. The reaction liquid was filtrated and the water content of the filtrate was measured by means of Karl Fisher's moisture meter and found to be 1259 ppm. The filtrate was concentrated and 1 L of ethyl acetate was added to the concentrate, followed by addition of hexane until crystals were precipitated. The resulting crystals were collected by filtration and dried to obtain the following compound (p25).

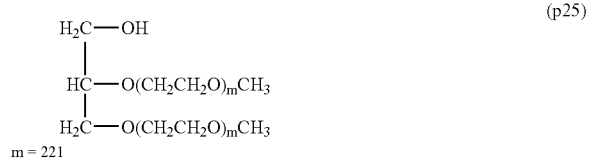

(p25)

m = 221

$^1$H-NMR (CDCl$_3$, internal standard: TMS) δ(ppm): 3.38 (6H, s, —CH$_3$), 3.40-3.80 (1773H, m, —C$\underline{H_2}$O(CH$_2$CH$_2$O)$_m$CH$_3$, C$\underline{H}$O(CH$_2$CH$_2$O)$_m$CH$_3$, CH$_2$OH). GPC analysis: <main peak> number average molecular weight (Mn): 18971, weight average molecular weight (Mw): 19204, polydispersity (Mw/Mn): 1.012, peak top molecular weight (Mp): 19687; <whole peak> number average molecular weight (Mn): 18811, weight average molecular weight (Mw): 19158, polydispersity (Mw/Mn): 1.018, peak top molecular weight (Mp): 19687.

Example 16-6

In Example 16-3, 2.0 kg of dry toluene was added to about 1 kg of the reaction liquid which remained in the autoclave. After 1.0 kg of toluene was removed by evaporation at an autoclave temperature of 95° C. under slight reduced pressure and then the atmosphere of the autoclave was replaced by nitrogen. After heating to 120° C., 1260 g of ethylene oxide was introduced under pressure thereto at 100 to 150° C. under a pressure of 1 MPa or lower, followed by continuation of the reaction for another 4 hours. After completion of the reaction, the whole was cooled to 70° C. and the reaction liquid was adjusted to pH 7.5 with 85% aqueous phosphoric acid solution to obtain the following compound (p26).

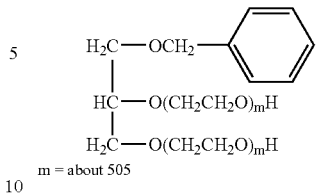

(p26)

m = about 505

$^1$H-NMR (CDCl$_3$, internal standard: TMS) δ(ppm): 3.40-3.80 (4045H, m, —C$\underline{H_2}$O(CH$_2$CH$_2$O)$_m$H, C$\underline{H}$O(CH$_2$CH$_2$O)$_m$H, CH$_2$OCH$_2$Ph), 4.54 (2H, s, —C$\underline{H_2}$Ph), 7.27-7.38 (5H, m, —CH$_2$P$\underline{h}$). GPC analysis: <main peak> number average molecular weight (Mn): 41830, weight average molecular weight (Mw): 42621, polydispersity (Mw/Mn): 1.019, peak top molecular weight (Mp): 44594; <whole peak> number average molecular weight (Mn): 40548, weight average molecular weight (Mw): 42059, polydispersity (Mw/Mn): 1.037, peak top molecular weight (Mp): 44594.

Example 16-7

Into a 2 L round-bottom flask fitted with a thermometer, a nitrogen-introducing tube, a stirrer, a Dean-stark tube, and a condenser tube were added 270 g (6 mmol) of the above compound (p26) and 1000 g of toluene, and the whole was heated under reflux to effect azeotropic removal of 200 g of toluene and water. After cooling to room temperature, 6.65 g (65.7 mmol) of triethylamine was added and the whole was heated to 40° C. Then, 4.51 g (39.4 mmol) of methanesulfonyl chloride was added thereto, followed by 3 hours of reaction at 40° C. After completion of the reaction, 25.3 g (131.4 mmol) of a 28% methanol solution of sodium methoxide was added to the reaction liquid, followed by 3 hours of reaction at 40° C. The pressure was reduced with maintaining the reaction liquid at 40° C. to remove about 200 g of a mixed solution of methanol/toluene by evaporation and then salts were removed by filtration. Then, 500 g of toluene was added to the filtrate and the mixture was transferred into a 2 L round-bottom flask fitted with a thermometer, a nitrogen-introducing tube, a stirrer, a Dean-stark tube, and a condenser tube. The whole was heated under reflux to effect azeotropic removal of 200 g of toluene and water. After cooling to room temperature, 6.65 g (65.7 mmol) of triethylamine was added and the whole was heated to 40° C. Then, 4.51 g (39.4 mmol) of methanesulfonyl chloride was again added thereto, followed by 3 hours of reaction at 40° C. After completion of the reaction, 25.3 g (131.4 mmol) of a 28% methanol solution of sodium methoxide was added to the reaction liquid, followed by 3 hours of reaction at 40° C. The pressure was reduced with maintaining the reaction liquid at 40° C. to remove about 200 g of a mixed solution of methanol/toluene by evaporation and then salts were removed by filtration. The filtrate was heated to 50° C. and then 200 g of 25% aqueous sodium chloride was added thereto. After stirring, the whole was left on standing and separated into layers and the lower aqueous layer was removed. The operation of washing with water was repeated twice. The upper toluene layer was dried over magnesium sulfate and then filtrated, and 1 L of ethyl acetate was added to the filtrate. Then, hexane was added thereto until crystals were precipitated. The crystals were collected by filtration and dried to obtain the following compound (p27).

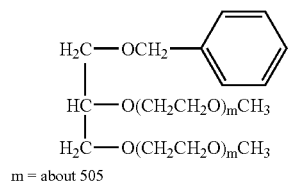

(p27)

m = about 505

¹H-NMR (CDCl₃, internal standard: TMS) δ(ppm): 3.38 (6H, s, —C$\underline{H}_3$), 3.40-3.80 (4045H, m, —C$\underline{H}_2$O(CH₂CH₂O)$_m\overline{CH}_3$, C$\underline{H}$O(CH₂CH₂O)$_m$CH₃, C$\underline{H}_2$OC$\underline{H}_2$Ph), 4.54 (2H, s, —C$\underline{H}_2$Ph), 7.27-7.38 (5H, m, —CH₂P$\underline{h}$). GPC analysis: <main peak> number average molecular weight (Mn): 42206, weight average molecular weight (Mw): 43056, polydispersity (Mw/Mn): 1.020, peak top molecular weight (Mp): 45057; <whole peak> number average molecular weight (Mn): 40990, weight average molecular weight (Mw): 42519, polydispersity (Mw/Mn): 1.037, peak top molecular weight (Mp): 45057.

Example 16-8

Into a pressure filter was charged 200 g of 5% palladium-carbon (50% hydrous product, manufactured by N. E. M. Cat.), and solvent substitution was carried out four times with 500 ml of anhydrous methanol under replacement by nitrogen to effect removal of water from the palladium-carbon. Into a 2 L round-bottom flask fitted with a thermometer, a nitrogen-introducing tube, a stirrer, and a condenser tube was added 100 g of the above compound (p27) and the whole amount of the palladium-carbon which had been subjected to solvent substitution. After replacement by nitrogen, 1200 ml of anhydrous methanol and 500 ml of cyclohexene were added thereto and the whole was heated to 30° C. to be allowed to react for 3.5 hours. The reaction liquid was filtrated and the water content of the filtrate was measured by means of Karl Fisher's moisture meter and found to be 2215 ppm. The filtrate was concentrated and 1 L of ethyl acetate was added to the concentrate, followed by addition of hexane until crystals were precipitated. The resulting crystals were collected by filtration and dried to obtain the following compound (p28).

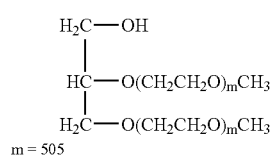

(p28)

m = 505

¹H-NMR (CDCl₃, internal standard: TMS) δ(ppm): 3.38 (6H, s, —C$\underline{H}_3$), 3.40-3.80 (4045H, m, —C$\underline{H}_2$O(CH₂CH₂O)$_m\overline{CH}_3$, C$\underline{H}$O(CH₂CH₂O)$_m$CH₃, C$\underline{H}_2$OH). GPC analysis: <main peak> number average molecular weight (Mn): 42121, weight average molecular weight (Mw): 42946, polydispersity (Mw/Mn): 1.020, peak top molecular weight (Mp): 45057; <whole peak> number average molecular weight (Mn): 41021, weight average molecular weight (Mw): 42450, polydispersity (Mw/Mn): 1.035, peak top molecular weight (Mp): 45057.

Example 17

Synthesis of Amino Compound (Group II(g)) (Case of R=Methyl Group, A¹O, A²O=Oxyethylene Group, n=0, and Molecular Weight=About 45000)

Example 17-1

Into a 500 ml round-bottom flask fitted with a thermometer, a nitrogen-introducing tube, a stirrer, and a condenser tube were added 70 g of the above compound (p28) and 70 g of ion-exchanged water, and the whole was heated to 40° C. to dissolve them. After dissolution, the solution was cooled to 10° C. or lower and 4.38 g of 50% aqueous potassium hydroxide solution was added thereto. Subsequently, 210 g of acrylonitrile was added dropwise over a period of 2 hours with maintaining a temperature of 5 to 10° C. After the dropwise addition, the reaction was continued for another 2 hours and 26.25 g of 8.5% aqueous phosphoric acid solution was added dropwise, followed by neutralization. After addition of 140 g of ion-exchanged water to the reaction liquid, the mixture was transferred into a separating funnel and 210 ml of ethyl acetate was added. After stirring, the whole was left on standing and the upper ethyl acetate layer was discarded. The extraction with ethyl acetate was repeated six times. After completion of the extraction, 65 g of sodium chloride was added to the aqueous layer and dissolved therein, and then the solution was extracted with 280 ml of chloroform. The resulting chloroform layer was dried over magnesium sulfate, filtrated, and then concentrated. Thereafter, 700 ml of ethyl acetate was added to the concentrate, which was dissolved therein. Then, hexane was added thereto until crystals were precipitated. The crystals were collected by filtration and again dissolved in 700 ml of ethyl acetate under heating. After cooling to room temperature, hexane was added thereto until crystals were precipitated. The crystals were collected by filtration and dried to obtain the following nitrile compound (p29).

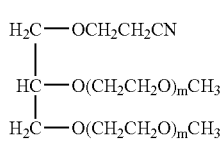

(p29)

m = 505

¹H-NMR (CDCl₃, internal standard: TMS) δ(ppm): 2.59-2.66 (2H, m, —C$\underline{H}_2$CH₂CN), 3.38 (6H, s, —C$\underline{H}_3$), 3.40-3.80 (4047H, m, —C$\underline{H}_2$O(CH₂CH₂O)$_m\overline{CH}_3$, C$\underline{H}$O(CH₂CH₂O)$_m$CH₃, C$\underline{H}_2$OC$\underline{H}_2$CH₂CN). GPC analysis: <main peak> number average molecular weight (Mn): 41849, weight average molecular weight (Mw): 42666, polydispersity (Mw/Mn): 1.020, peak top molecular weight (Mp): 44594; <whole peak> number average molecular weight (Mn): 40271, weight average molecular weight (Mw): 41980, polydispersity (Mw/Mn): 1.042, peak top molecular weight (Mp): 44594.

Example 17-2

To a 1 L autoclave were added 50 g of the nitrile compound of the formula (p29), 500 g of toluene, and 4.5 g of nickel (manufactured by N. E. M. Cat., 5136p), and the whole was heated to 60° C. The autoclave was pressurized with ammonia until the inner pressure reached 0.7 MPa and then with hydrogen until the inner pressure reached 4.5 MPa, followed by 3 hours of reaction at 130° C. After the reaction, the reaction liquid was cooled to 70° C., and purge with nitrogen was repeated until ammonia smell disappeared. The whole amount of the reaction liquid was taken out and filtrated. After cooling of the filtrate to room temperature, hexane was added until crystals were precipitated. The crystals were collected by filtration and dried to obtain the following amine compound (p30).

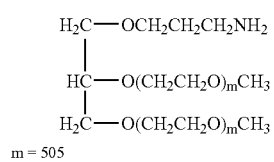

$^1$H-NMR (CDCl$_3$, internal standard: TMS) δ(ppm): 1.82-1.90 (2H, m, —CH$_2$CH$_2$CH$_2$NH$_2$), 2.90-2.97 (2H, m, —CH$_2$CH$_2$CH$_2$NH$_2$), 3.38 (6H, s, —CH$_3$), 3.40-3.80 (4047H, m, —CH$_2$O(CH$_2$CH$_2$O)$_m$CH$_3$, CHO(CH$_2$CH$_2$O)$_m$CH$_3$, CH$_2$O CH$_2$CH$_2$CH$_2$NH$_2$).

Example 18

Synthesis of Maleimide Compound (Group I(e)) (Case of R=Methyl Group, A$^1$O, A$^2$O=Oxyethylene Group, n=0, and Molecular Weight=About 45000)

Into a 300 ml round-bottom flask fitted with a thermometer, a nitrogen-introducing tube, a stirrer, and a condenser tube were added 45 g (1 mmol) of the compound (p30), 42 ml of acetonitrile, and 84 ml of toluene, and the whole was heated at 40° C. to dissolve them. After cooling to room temperature, 0.51 g (5 mmol) of N-methylmorpholine and 399 mg (1.5 mmol) of N-succinimidyl 3-maleimidopropionate were added thereto under light shielding, followed by 3.5 hours of reaction. After filtration of the reaction liquid, 840 ml of ethyl acetate was added and hexane was added thereto until crystals were precipitated. The crystals were collected by filtration and 42 ml of acetonitrile and 840 ml of ethyl acetate were added. After dissolution under heating, hexane was added until crystals were precipitate. Then, the crystals were collected by filtration and dried to obtain the following compound (p31).

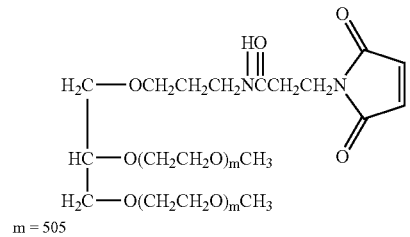

$^1$H-NMR (CDCl$_3$, internal standard: TMS) δ(ppm): 1.70-1.78 (2H, m, —CH$_2$CH$_2$CH$_2$N), 2.45-2.53 (2H, m, —NHCOCH$_2$CH$_2$N), 3.38 (6H, s, —CH$_3$), 3.40-3.80 (4051H, m, —CH$_2$O(CH$_2$CH$_2$O)$_m$CH$_3$, CHO(CH$_2$CH$_2$O)$_m$CH$_3$, CH$_2$O CH$_2$CH$_2$CH$_2$NHCOCH$_2$CH$_2$), 6.44 (1H, m, NHCO), 6.71 (2H, s, —CH═CH—). GPC analysis: <main peak> number average molecular weight (Mn): 41918, weight average molecular weight (Mw): 42709, polydispersity (Mw/Mn): 1.019, peak top molecular weight (Mp): 44594, <whole peak> number average molecular weight (Mn): 40231, weight average molecular weight (Mw): 42602, polydispersity (Mw/Mn): 1.059, peak top molecular weight (Mp): 44594.

Example 19

Synthesis of Succinimide Compound (Group I(a)) (Case of R=Methyl Group, A$^1$O, A$^2$O=Oxyethylene Group, n=0, and Molecular Weight=About 20000)

Into a 200 ml round-bottom flask fitted with a thermometer, a nitrogen-introducing tube, a stirrer, a Dean-stark tube, and a condenser tube were charged 10 g (0.5 mmol) of the compound (p25), 0.1 g of sodium acetate, and 100 ml of toluene, and the whole was refluxed to effect removal of water. Then, 285 mg (2.5 mmol) of glutaric anhydride was added to the reaction liquid, followed by 12 hours of reaction at 110° C. After cooling of the reaction liquid, 518 mg (4.5 mmol) of N-hydroxysuccinimide and 934 mg (4.55 mmol) of DCC were added thereto, followed by 2 hours of reaction at 40° C. The reaction liquid was filtered and then hexane was added until crystals were precipitated. The crystals were collected by filtration and again dissolved in 100 ml of ethyl acetate and 10 ml of acetonitrile. Then, hexane was added to the solution until crystals were precipitated. The crystals were collected by filtration and dried to obtain the following succinimide compound (p32).

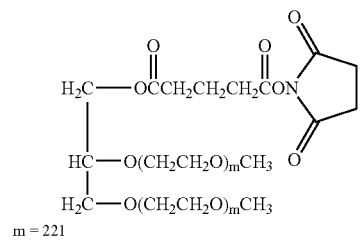

$^1$H-NMR (CDCl$_3$, internal standard: TMS) δ(ppm): 2.07 (2H, m, —OCOCH$_2$CH$_2$CH$_2$COON—), 2.50 (2H, t, —OCOCH$_2$CH$_2$CH$_2$COON—), 2.72 (2H, t, —OCOCH$_2$CH$_2$ $CH_2COON$—), 2.84 (4H, s, succinimide), 3.38 (6H, s, —$\underline{CH}_3$), 3.40-3.80 (1771H, m, —$\underline{CH_2}O(CH_2CH_2O)_mCH_3$, $\underline{CHO}(CH_2CH_2O)_mCH_3$), 4.10-4.30 (2H, m, —$\underline{CH_2}OCOCH_2CH_2COON$—).

Example 20

To a 300 ml round-bottom flask fitted with a thermometer, a nitrogen-introducing tube, and a stirrer were added 27.3 g (0.15 mol) of 3-benzyloxy-1,2-propanediol, 135 g of dry toluene, and 0.9 g (39 mmol: 26 mol %) of sodium. With introduction of nitrogen thereinto, the whole was stirred at 80° C. until sodium dissolved. After dissolution, the solution was further stirred at 80° C. for 2 hours.

The reaction liquid was charged into a 5 L autoclave thoroughly dried beforehand and the same operations as in Examples 16-3, 16-6, 16-7, and 16-8 were conducted to obtain the compound (p33) having the same structure as that of (p28).

Example 21

The solution of 3-benzyloxy-1,2-propanediol alcoholated with sodium in Example 1-3, the solution of 3-benzyloxy-1,2-propanediol alcoholated with sodium in Example 16-3, and the solution of 3-benzyloxy-1,2-propanediol alcoholated with sodium before charging into the autoclave in Example 20 were sampled and converted into derivatives under the following conditions, and then they were measured by gas chromatography (GC). The results are shown in Table 3.

Each sample was weighed in an amount of 0.2 g and dissolved with adding 1.0 ml of pyridine, and then 0.8 ml of hexamethyldisilazane was added thereto. To the solution was added 0.4 ml of chlorotrimethylsilane, followed by 30 minutes of stirring. The reaction liquid was filtrated through a syringe filter (PTFE, 0.45 μm) and GC measurement was conducted under the following conditions:

GC system: HP6890, column: HP-5 (0.25 μm×30 cm), detector: FID, injection temperature: 320° C., injection: splitless, injection amount: 0.2 μl, carrier gas: helium, flow rate: 23 cm/sec, column temperature 80° C. (0 min)→15° C./min→320° C. 24 min), detector temperature: 320° C.

TABLE 3

|  | Benzyl alcohol | Glycerin |
| --- | --- | --- |
| Example 1-3 | 0% | 0.4% |
| Example 16-3 | 0% | 0.3% |
| Example 20 | 2.2% | 1.3% |

From the results of Table 3, it was found that benzyl alcohol which causes formation of reactive low-molecular-weight impurities and glycerin which causes formation of non-reactive high-molecular-weight impurities were hardly produced under the treating conditions with sodium as in Examples 1-3 and 16-3.

Example 22

Into a 200 ml round-bottom flask fitted with a thermometer, a nitrogen-introducing tube, a stirrer, a Dean-stark tube, and a condenser tube were added 10 g (1 mmol) of the compound (p2) obtained in Example 1-4 and 50 g of toluene, and the whole was heated under reflux to effect azeotropic removal of water. After cooling to room temperature, 2.02 g (20 mmol) of triethylamine was added thereto and the whole was heated to 40° C. Then, 0.687 g (6 mmol) of methanesulfonyl chloride were added thereto, followed by 3 hours of reaction at 40° C. After completion of the reaction, hydrochloride salt was removed by filtration and 100 ml of ethyl acetate was added to the filtrate, followed by addition of hexane until crystals were precipitated. The resulting crystals were collected by filtration and the crystals were dissolved in 200 ml of ethyl acetate under heating. After cooling to room temperature, hexane was added until crystals were precipitated. The crystals were collected by filtration and dried. Then, 20 mg of the resulting crystals was sampled and dissolved in deuterated chloroform, and $^1$H-nuclear magnetic resonance measurement was conducted (integration: 128 times) to obtain a spectrum. At that time, Mme was 6 and Mms was 0.073.

Example 23

Using 10 g (0.5 mmol) of the compound (p12) obtained in Example 7-2, 1.01 g (10 mmol) of triethylamine, and 0.344 g (3 mmol) of methanesulfonyl chloride, the same operations as in Example 22 were conducted. Then, $^1$H-nuclear magnetic resonance measurement was conducted (integration: 256 times) to obtain a spectrum. At that time, Mme was 6 and Mms was 0.102.

Example 24

Using 10 g (0.5 mmol) of the compound (p24) which had been twice alkyl-etherified in Example 16-4, 1.01 g (10 mmol) of triethylamine, and 0.344 g (3 mmol) of methanesulfonyl chloride, the same operations as in Example 22 were conducted. Then, $^1$H-nuclear magnetic resonance measurement was conducted (integration: 256 times) to obtain a spectrum. At that time, Mme was 6 and Mms was 0.019.

Example 25

Using 11.3 g (0.25 mmol) of the compound (p27) which had been twice alkyl-etherified in Example 16-7, 0.506 g (5 mmol) of triethylamine, and 0.172 g (1.5 mmol) of methanesulfonyl chloride, the same operations as in Example 22 were conducted. Then, $^1$H-nuclear magnetic resonance measurement was conducted (integration: 256 times) to obtain a spectrum. At that time, Mme was 6 and Mms was 0.026.

Example 26

Using Mme, Mms, and peak top molecular weight (Mp) obtained in each of Examples 22 to 25, Hrd and Hrd/Mp× 1000000 were calculated. As the peak top molecular weight, each data of (p3), (p13), (p25), and (p28) was used. The results are shown in Table 4. As a result, it was revealed that the ratio of alkyl-etherification of the compound represented by the formula (p) of the invention was high and, in the case that the alkyl-etherification was repeated, the conversion was even higher and the hydroxyl group remained only a little.

TABLE 4

|  | Hrd | Mp | Hrd/Mp × 1000000 |
| --- | --- | --- | --- |
| Example 22 | 0.0120 | 10351 | 1.16 |
| Example 23 | 0.0167 | 18989 | 0.88 |
| Example 24 | 0.0032 | 19687 | 0.16 |
| Example 25 | 0.0043 | 45057 | 0.10 |

Example 27

Into a 200 ml round-bottom flask fitted with a thermometer, a nitrogen-introducing tube, a stirrer, a Dean-stark tube, and a condenser tube were added 10 g (1 mmol) of the compound (p3) obtained in Example 1-5 and 50 g of toluene, and the whole was heated under reflux to effect azeotropic removal of water. After cooling to room temperature, 2.02 g (20 mmol) of triethylamine was added thereto and the whole was heated to 40° C. Then, 0.687 g (6 mmol) of methanesulfonyl chloride were added thereto, followed by 3 hours of reaction at 40° C. After completion of the reaction, hydrochloride salt was removed by filtration and 100 ml of ethyl acetate was added to the filtrate, followed by addition of hexane until crystals were precipitated. The resulting crystals were collected by filtration and the crystals were dissolved in 200 ml of ethyl acetate under heating. After cooling to room temperature, hexane was added until crystals were precipitated. The crystals were collected by filtration and dried. Then, 20 mg of the resulting crystals was sampled and dissolved in deuterated methanol, and $^1$H-nuclear magnetic resonance measurement was conducted (integration: 128 times) to obtain a spectrum. At that time, when M1 detected at 3.132 ppm was regarded as 3, M2 detected at 3.117 ppm was 0.295.

Example 28

Using 10 g (0.5 mmol) of the compound (p25) obtained in Example 16-5, 1.01 g (10 mmol) of triethylamine, and 0.344 g (3 mmol) of methanesulfonyl chloride, the same operations as in Example 27 were conducted. Then, $^1$H-nuclear magnetic resonance measurement was conducted (integration: 256 times) to obtain a spectrum. At that time, M1 was 3 and M2 was 0.091.

Example 29

Using 11.3 g (0.25 mmol) of the compound (p28) obtained in Example 16-8, 0.51 g (5 mmol) of triethylamine, and 0.172 g (1.5 mmol) of methanesulfonyl chloride, the same operations as in Example 27 were conducted. Then, $^1$H-nuclear magnetic resonance measurement was conducted (integration: 256 times) to obtain a spectrum. At that time, M1 was 3 and M2 was 0.112.

Example 30

Using 11.3 g (0.25 mmol) of the compound (p33) obtained in Example 20, 0.51 g (5 mmol) of triethylamine, and 0.172 g (1.5 mmol) of methanesulfonyl chloride, the same operations as in Example 27 were conducted. Then, $^1$H-nuclear magnetic resonance measurement was conducted (integration: 256 times) to obtain a spectrum. At that time, M1 was 3 and M2 was 0.212.

Example 31

From M1 and M2 obtained in each of Examples 27 to 30, M2/(M1+M2)×100 was calculated. The results are shown in Table 5. As a result, it was revealed that the compounds of the invention each had a high purity. Also, from the results of Examples 29 and 30, it was found that higher purity was achieved by carrying out the alcoholation of the compound represented by the formula (9) with the temperature being lowered.

TABLE 5

| | M1 | M2 | M2/(M1 + M2) × 100 |
|---|---|---|---|
| Example 27 | 3 | 0.295 | 8.95 |
| Example 28 | 3 | 0.091 | 2.94 |
| Example 29 | 3 | 0.112 | 3.60 |
| Example 30 | 3 | 0.212 | 6.60 |
| Example 32 | 3 | 0.162 | 5.12 |

Example 32

Into a 2 L round-bottom flask fitted with a thermometer, a nitrogen-introducing tube, a stirrer, and a condenser tube were added 100 g of the above compound (p27) and 200 g of 5% palladium-carbon (50% hydrous product, manufactured by N. E. M. Cat.) as the hydrous product, and debenzylation was carried out in the same manner as in Example 16-8 to obtain the compound (p34) having the same structure as that of (p28). At that time, the water content in the reaction system was measured by means of Karl Fisher's moisture meter and found to be 4.17%.

Using 11.3 g (0.25 mmol) of the resulting compound (p34), 0.51 g (5 mmol) of triethylamine, and 0.172 g (1.5 mmol) of methanesulfonyl chloride, the same operations as in Example 27 were conducted. Then, $^1$H-nuclear magnetic resonance measurement was conducted (integration: 256 times) to obtain a spectrum. At that time, M1 was 3 and M2 was 0.162.

As shown in Table 5, from the results of Examples 29 and 32, it was found that more highly pure compound of the formula (p) could be obtained by reducing the water content in the reaction system to 1% or lower.

Example 33

Modification of Peptide

Figure 6:
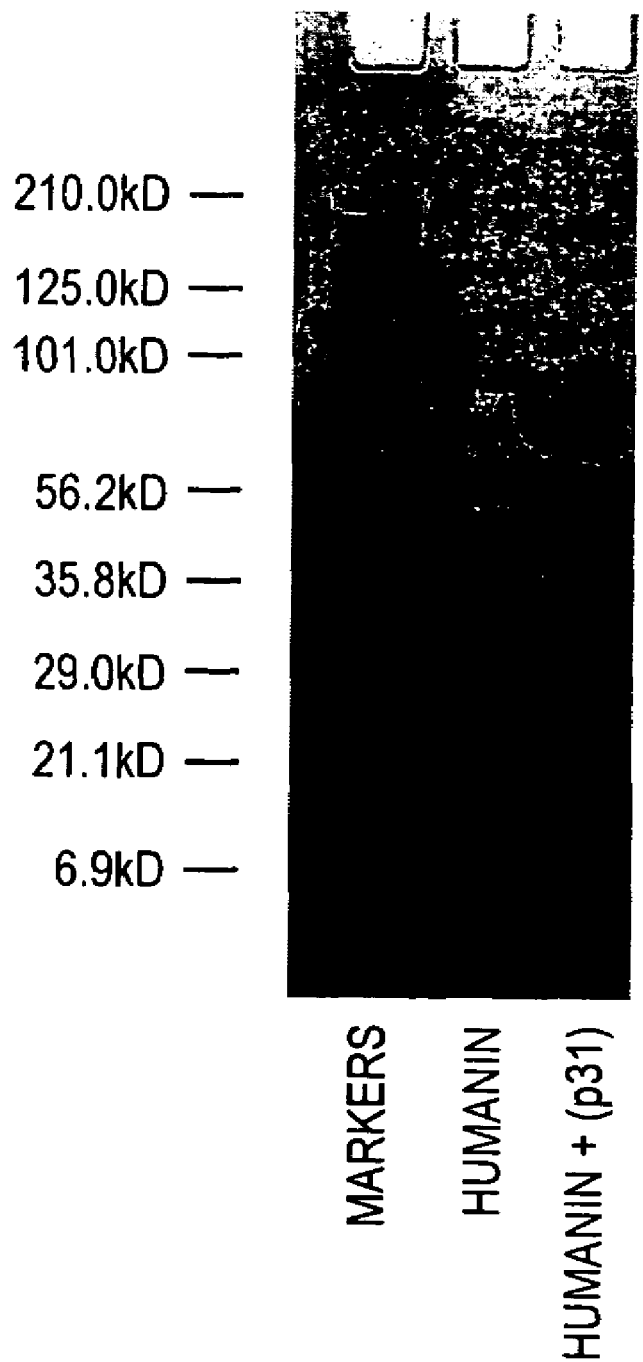
FIG. 6 is a result of electrophoresis of the compound obtained by modifying Humanin with the compound (p31).

A peptide of Humanin (Met-Ala-Pro-Arg-Gly-Phe-Ser-Cys-Leu-Leu-Leu-Leu-Thr-Ser-Glu-Ile-Asp-Leu-Pro-Val-Lys-Arg-Arg-Ala) (molecular weight 2687.2) was adjusted to 0.5 μM with 10 mM phosphate buffer (pH=6.4). Into 200 μl of the solution was added 4 mg of the compound of the formula (p31), followed by 4 hours of reaction at room temperature. Then, 200 μl of the reaction liquid was charged into a SP-Sepharose FF (manufactured by Amersham) column, which was then equilibrated with 20 mM Tris-HCl buffer (pH=8.2). After the equilibration, a solution obtained by adding NaCl to the buffer so as to be 1N was passed through the column and a fraction of the peptide modified with (p31) was obtained with monitoring the elute by UV. Thereafter, 20 μl of the fraction was mixed with 20 μl of a Tris-SDS sample-treating liquid, followed by heating on a boiling water bath for 2 minutes and 30 seconds. Then, 20 μl of the solution was analyzed by sodium dodecyl sulfate-polyacrylamide gel electrophoresis (4-20%). The staining was carried out by CBB staining. The results were shown in FIG. 6.

As a result, it was found that the mercapto group (cysteine) of the peptide reacted with the maleimide of (p31), thereby modification was achieved.

Example 34

Synthesis of Succinimide Compound (Group I(a)) (Case of R=Methyl Group, A$^1$O, A$^2$O=Oxyethylene Group, n=0, and Molecular Weight=About 45000)

Into a 200 ml round-bottom flask fitted with a thermometer, a nitrogen-introducing tube, a stirrer, a Dean-stark tube, and a condenser tube were charged 11.3 g (0.25 mmol) of the compound (p28), 0.1 g of sodium acetate, and 100 ml of toluene, and the whole was refluxed to effect removal of water. Then, 285 mg (2.5 mmol) of glutaric anhydride was added to the reaction liquid, followed by 12 hours of reaction at 110° C. After cooling of the reaction liquid, 518 mg (4.5 mmol) of N-hydroxysuccinimide and 934 mg (4.55 mmol) of DCC were added thereto, followed by 2 hours of reaction at 40° C. The reaction liquid was filtered and then hexane was added until crystals were precipitated. The crystals were collected by filtration and again dissolved in 200 ml of ethyl acetate and 20 ml of acetonitrile. Then, hexane was added to the solution until crystals were precipitated. The crystals were collected by filtration and dried to obtain the following succinimide compound (p35).

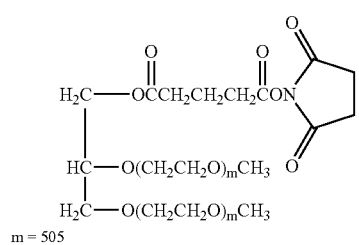

(p35)

m = 505

$^1$H-NMR (CDCl$_3$, internal standard: TMS) δ(ppm): 2.07 (2H, m, —OCOCH$_2$CH$_2$CH$_2$COON—), 2.50 (2H, t, —OCO CH$_2$CH$_2$CH$_2$COON—), 2.72 (2H, t, —OCOCH$_2$CH$_2$ CH$_2$COON—), 2.84 (4H, s, succinimide), 3.38 (6H, s, —CH$_3$), 3.40-3.80 (4043H, m, —CH$_2$O(CH$_2$CH$_2$O)$_m$CH$_3$, CHO(CH$_2$CH$_2$O)$_m$CH$_3$), 4.10-4.30 (2H, m, —CH$_2$OCOCH$_2$CH$_2$CH$_2$COON—).

Example 35

Modification of Insulin

Using the succinimide of (p32) obtained in Example 19 and the succinimide of (p35) obtained in Example 34, insulin (recombinant human insulin, Mw 5800, manufactured by SEROLOGICALS CORPORATION) was modified.

Using 0.1N sodium carbonate buffer (pH=9.0), a 10 mg/ml buffer solution of the insulin was prepared. Into 100 μl of the solution was added 6.8 mg of the compound of the formula (p32), followed by 20 hours of reaction at 4° C. Then, the whole amount of the reaction liquid was charged into a Q-Sepharose FF (manufactured by Amersham) column, which was then equilibrated with 20 mM Tris-HCl buffer (pH=8.2). After the equilibration, a solution obtained by adding NaCl to the buffer so as to be 1N was passed through the column and a fraction of the peptide modified with (p32) was obtained with monitoring the elute by UV. Thereafter, 20 μl of the fraction was mixed with 20 μl of a Tris-SDS sample-treating liquid, followed by heating on a boiling water bath for 2 minutes and 30 seconds. Then, 20 μl of the solution was analyzed by sodium dodecyl sulfate-polyacrylamide gel electrophoresis (4-20%). The staining was carried out by CBB staining.

Similarly, in the case of (p35), 13.6 mg of the compound of the formula (p35) was added to 100 μl of a 10 mg/ml buffer solution of the insulin and the whole was treated in a similar manner.

Figure 7:
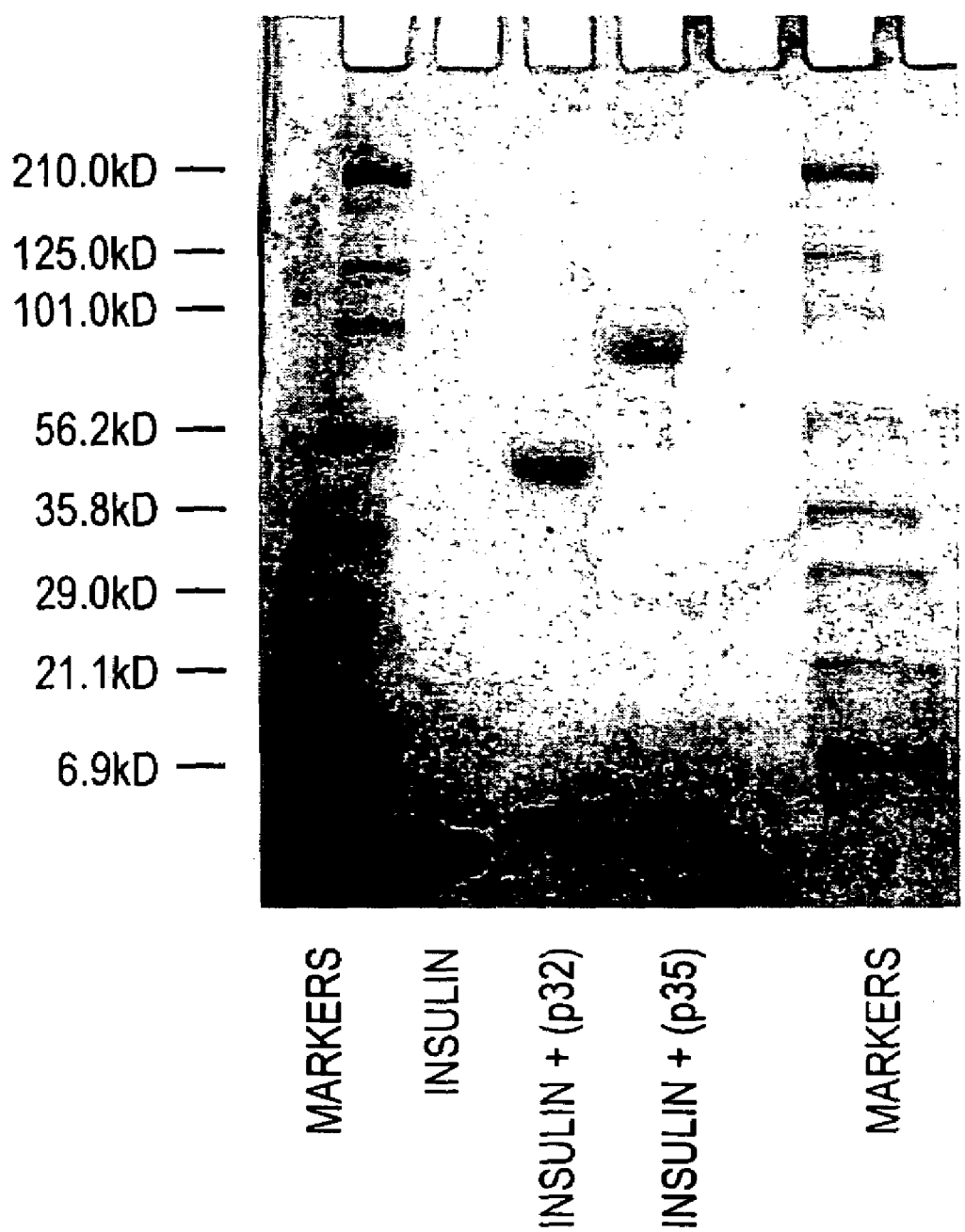
FIG. 7 is a result of electrophoresis of the compound obtained by modifying insulin with the compound (p32) or (p35).

The results were shown in FIG. 7. As a result, it was found that the insulin was modified with the compound of the formula (p32) or (p35).

---

---

What is claimed is:

1. A modified bio-related substance, comprising a bio-related substance and at least one poly(alkylene glycol)oxy group bonded to said bio-related substance, said at least one poly(alkylene glycol)oxy group being represented by the following formula (1):

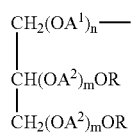

(1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, and the groups represented by $OA^2$ are the same or different from each other in one molecule, n and m are each average number of moles of the oxyalkylene group added, n represents 0 to 1000, and m represents 10 to 1000, wherein said modified bio-related substance is formed by reacting a functional group X of an intermediate represented by formula (2) with a functional group of the bio-related substance:

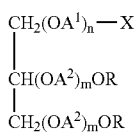
(2)

wherein X is at least one selected from the group consisting of (a), (b), (c), (d), (e), (f), (g), (h), (i), (j), (k), (xx1), (xx2) and (xx3):

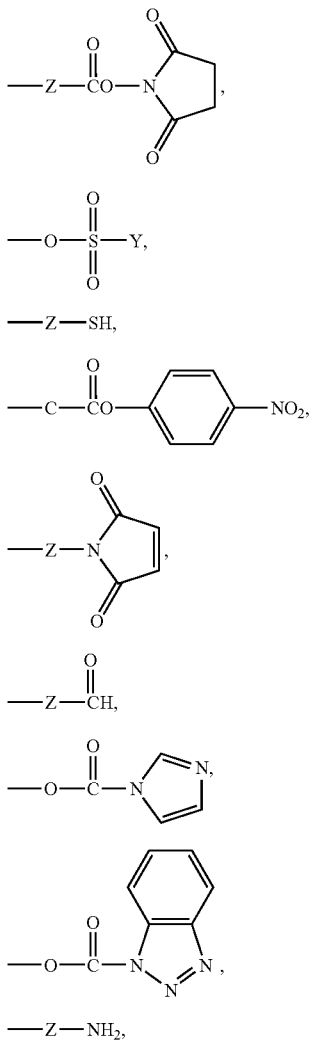

(j)

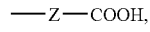
(k)

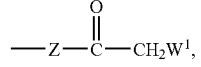
(xx1)

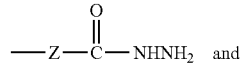
(xx2)

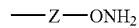
(xx3)

wherein Z represents a linking group containing an alkylene group or an alkylene group containing an ether bond, an ester bond, a urethane bond, an amide bond, a carbonate bond, or a secondary amino group and Y represents a hydrocarbon group having 1 to 10 carbon atoms which may contain fluorine atom(s); and $W^1$ represents a halogen atom selected from Cl, Br and I.

2. The modified bio-related substance according to claim 1, wherein in the formula (1), R is a hydrocarbon group having 1 to 10 carbon atoms, $OA^1$ and $OA^2$ are each an oxyalkylene group having 2 to 3 carbon atoms, n is 0 to 500, and m is 10 to 1000.

3. The modified bio-related substance according to claim 1, wherein in the formula (1), R is a methyl group, $OA^1$ and $OA^2$ are each an oxyethylene group, n is 0 to 50, and m is 20 to 800.

4. The modified bio-related substance according to claim 1, wherein in the formula (1), n is 0.

5. The modified bio-related substance according to claim 1, wherein in the formula (1), n is 1 to 50.

6. The modified bio-related substance according to claim 1, wherein the bio-related substance has a physiological activity on a body.

7. The modified bio-related substance according to claim 1, wherein the bio-related substance is a protein or a polypeptide.

8. The modified bio-related substance according to claim 1, wherein the bio-related substance is an anticancer drug.

9. The modified bio-related substance according to claim 1, wherein the bio-related substance is an antifungal drug.

10. The modified bio-related substance according to claim 1, wherein the bio-related substance is a phospholipid.

11. The modified bio-related substance according to claim 3, wherein in the formula (1), n is 0.

12. The modified bio-related substance according to claim 3, wherein in the formula (1), n is 1 to 50.

13. The modified bio-related substance according to claim 11, wherein the bio-related substance has a physiological activity on a body.

14. The modified bio-related substance according to claim 11, wherein the bio-related substance is a protein or a polypeptide.

15. The modified bio-related substance according to claim 11, wherein the bio-related substance is an anticancer drug.

16. The modified bio-related substance according to claim 11, wherein the bio-related substance is an antifungal drug.

17. The modified bio-related substance according to claim 11, wherein the bio-related substance is a phospholipid.

18. The modified bio-related substance according to claim 12, wherein the bio-related substance has a physiological activity on a body.

19. The modified bio-related substance according to claim 12, wherein the bio-related substance is a protein or a polypeptide.

20. The modified bio-related substance according to claim 12, wherein the bio-related substance is an anticancer drug.

21. The modified bio-related substance according to claim 12, wherein the bio-related substance is an antifungal drug.

22. The modified bio-related substance according to claim 12, wherein the bio-related substance is a phospholipid.

23. The modified bio-related substance according to claim 1, wherein the functional group of the bio-related substance is selected from the group consisting of an amino group, a mercapto group, a carboxyl group, an aldehyde group and a group containing an unsaturated bond.

24. The modified bio-related substance according to claim 1, wherein X is selected from the group consisting of (a), (b), (d), (f), (h), (i) and (k) and the functional group of the bio-related substance is an amino group.

25. The modified bio-related substance according to claim 1, wherein X is selected from the group consisting of (a), (b), (c), (d), (e), (f), (h), (i), (k) and (xx1) and the functional group of the bio-related substance is a mercapto group.

26. The modified bio-related substance according to claim 1, wherein X is represented by (c) and the functional group of the bio-related substance contains an unsaturated bond.

27. The modified bio-related substance according to claim 1, wherein X is selected from the group consisting of (c), (g) and (j) and the functional group of the bio-related substance is a carboxyl group.

28. The modified bio-related substance according to claim 1, wherein X is selected from the group consisting of (c), (g), (j), (xx2) and (xx3) and the functional group of the bio-related substance is an aldehyde group.

29. The modified bio-related substance according to claim 1, wherein Z represents a linking group selected from the group consisting of an alkylene group, an alkylene group containing an ether bond, an alkylene group containing an ester bond, an alkylene group containing a urethane bond, an alkylene group containing an amide bond, an alkylene group containing a carbonate bond and an alkylene containing a secondary amino group.

* * * * *